US008814788B2

(12) United States Patent
Gan

(10) Patent No.: US 8,814,788 B2
(45) Date of Patent: Aug. 26, 2014

(54) SUCTION RETRACTOR

(75) Inventor: Philip Gan, Warrnambol Victoria (AU)

(73) Assignee: Livac Pty Ltd, Warrnambool (AU)

( * ) Notice: Subject to any disclaimer, the term of this patent is extended or adjusted under 35 U.S.C. 154(b) by 0 days.

(21) Appl. No.: 13/697,470

(22) PCT Filed: May 13, 2011

(86) PCT No.: PCT/AU2011/000567
§ 371 (c)(1),
(2), (4) Date: Dec. 12, 2012

(87) PCT Pub. No.: WO2011/140612
PCT Pub. Date: Nov. 17, 2011

(65) Prior Publication Data
US 2013/0109924 A1    May 2, 2013

(30) Foreign Application Priority Data

May 13, 2010  (AU) ................................ 2010902064

(51) Int. Cl.
*A61B 1/32* (2006.01)
(52) U.S. Cl.
USPC .......................................... 600/206; 600/233
(58) Field of Classification Search
USPC .................. 606/201, 205–208, 233; 600/201, 600/205–208, 233
See application file for complete search history.

(56) References Cited
U.S. PATENT DOCUMENTS 2,548,602 A * 4/1951 Greenburg ..................... 600/207
3,592,198 A * 7/1971 Evans ............................ 606/124
3,768,477 A * 10/1973 Anders et al. ................... 433/91
3,863,639 A * 2/1975 Kleaveland ................... 128/850
3,976,054 A * 8/1976 Evans ............................ 600/187
4,053,984 A * 10/1977 Moss ............................. 433/93

(Continued)

FOREIGN PATENT DOCUMENTS

WO       00/48516 A1    8/2000
WO       00/62680 A1   10/2000

(Continued)

OTHER PUBLICATIONS

PCT International Preliminary Report on Patentability, PCT International Application No. PCT/AU2011/000567, dated Dec. 22, 2011; 4 pp.

(Continued)

*Primary Examiner* — Pedro Philogene
*Assistant Examiner* — Lynnsy Schneider
(74) *Attorney, Agent, or Firm* — Hoffmann & Baron, LLP

(57) ABSTRACT

The subject invention provides a suction retractor comprising a flexible continuous dam which forms a closed loop of any shape and which defines one or more inlet opening into an interior of the closed loop, so that suction can be applied into an interior of the continuous dam. The suction retractor may further comprise a suction tube defining a suction channel, the suction tube attached to or attachable to the continuous dam and when attached the suction channel continuous with the one or more inlet. The one or more inlet may open to a continuous channel extending throughout an interior of the closed loop. Preferably, the continuous dam is planar or substantially planar and comprises a first compacted configuration for insertion and a second open configuration for retraction. The suction retractor of the invention finds application in single incision and convention laparoscopic surgery.

26 Claims, 20 Drawing Sheets

(56) References Cited

U.S. PATENT DOCUMENTS

| | | | |
|---|---|---|---|
| 4,802,851 A * | 2/1989 | Rhoades | 433/93 |
| 4,889,107 A * | 12/1989 | Kaufman | 600/206 |
| 5,015,243 A * | 5/1991 | Schifano | 604/315 |
| 5,159,921 A * | 11/1992 | Hoover | 600/207 |
| 5,309,896 A * | 5/1994 | Moll et al. | 600/207 |
| 5,353,786 A * | 10/1994 | Wilk | 600/249 |
| 5,402,772 A * | 4/1995 | Moll et al. | 600/207 |
| 5,425,357 A * | 6/1995 | Moll et al. | 600/207 |
| 5,450,843 A * | 9/1995 | Moll et al. | 600/207 |
| 5,454,367 A * | 10/1995 | Moll et al. | 600/207 |
| 5,465,711 A * | 11/1995 | Moll et al. | 600/207 |
| 5,522,791 A * | 6/1996 | Leyva | 600/207 |
| 5,527,264 A * | 6/1996 | Moll et al. | 600/204 |
| 5,545,123 A * | 8/1996 | Ortiz et al. | 600/235 |
| 5,556,417 A * | 9/1996 | Sher | 600/236 |
| 5,562,603 A * | 10/1996 | Moll et al. | 600/204 |
| 5,575,759 A * | 11/1996 | Moll et al. | 600/207 |
| 5,735,791 A * | 4/1998 | Alexander et al. | 600/37 |
| 5,738,629 A * | 4/1998 | Moll et al. | 600/116 |
| 5,743,850 A * | 4/1998 | Moll et al. | 600/204 |
| 5,743,851 A * | 4/1998 | Moll et al. | 600/204 |
| 5,762,606 A * | 6/1998 | Minnich | 600/205 |
| 5,807,243 A * | 9/1998 | Vierra et al. | 600/204 |
| 5,823,945 A * | 10/1998 | Moll et al. | 600/204 |
| 5,836,311 A * | 11/1998 | Borst et al. | 128/897 |
| 5,865,728 A * | 2/1999 | Moll et al. | 600/204 |
| 5,885,271 A * | 3/1999 | Hamilton et al. | 606/1 |
| 5,927,284 A * | 7/1999 | Borst et al. | 128/898 |
| 6,007,523 A * | 12/1999 | Mangosong | 604/284 |
| 6,015,378 A | 1/2000 | Borst et al. | |
| 6,033,426 A * | 3/2000 | Kaji | 606/213 |
| 6,042,539 A * | 3/2000 | Harper et al. | 600/201 |
| 6,083,155 A * | 7/2000 | Trese | 600/236 |
| 6,090,041 A * | 7/2000 | Clark et al. | 600/205 |
| 6,139,492 A * | 10/2000 | Vierra et al. | 600/204 |
| 6,159,201 A * | 12/2000 | Hamilton et al. | 606/1 |
| 6,162,172 A * | 12/2000 | Cosgrove et al. | 600/208 |
| 6,190,311 B1 * | 2/2001 | Glines et al. | 600/208 |
| 6,210,323 B1 * | 4/2001 | Gilhuly et al. | 600/210 |
| 6,241,658 B1 * | 6/2001 | Goodrich | 600/210 |
| 6,267,751 B1 * | 7/2001 | Mangosong | 604/284 |
| 6,338,712 B2 * | 1/2002 | Spence et al. | 600/201 |
| 6,346,077 B1 * | 2/2002 | Taylor et al. | 600/204 |
| 6,371,968 B1 * | 4/2002 | Kogasaka et al. | 606/190 |
| 6,383,134 B1 * | 5/2002 | Santilli | 600/205 |
| 6,406,424 B1 * | 6/2002 | Williamson et al. | 600/201 |
| 6,447,443 B1 * | 9/2002 | Keogh et al. | 600/37 |
| 6,478,029 B1 * | 11/2002 | Boyd et al. | 128/898 |
| 6,482,151 B1 * | 11/2002 | Vierra et al. | 600/204 |
| 6,506,149 B2 * | 1/2003 | Peng et al. | 600/37 |
| 6,517,563 B1 * | 2/2003 | Paolitto et al. | 606/205 |
| 6,558,371 B2 * | 5/2003 | Dorn | 606/1 |
| 6,589,166 B2 * | 7/2003 | Knight et al. | 600/205 |
| 6,605,037 B1 * | 8/2003 | Gresl et al. | 600/204 |
| 6,620,098 B1 * | 9/2003 | Milverton | 600/236 |
| 6,656,109 B2 | 12/2003 | DeVries et al. | |
| 6,730,020 B2 * | 5/2004 | Peng et al. | 600/201 |
| 6,743,169 B1 * | 6/2004 | Taylor et al. | 600/204 |
| 6,746,471 B2 * | 6/2004 | Mortier et al. | 606/207 |
| 6,764,444 B2 * | 7/2004 | Wu et al. | 600/206 |
| 6,767,323 B2 * | 7/2004 | Martinez | 600/205 |
| 6,773,418 B1 * | 8/2004 | Sharrow et al. | 604/176 |
| 6,796,940 B2 * | 9/2004 | Bonadio et al. | 600/206 |
| 6,875,171 B2 * | 4/2005 | Paolitto et al. | 600/205 |
| 6,893,394 B2 * | 5/2005 | Douglas et al. | 600/205 |
| 6,899,670 B2 * | 5/2005 | Peng et al. | 600/37 |
| 6,936,002 B2 * | 8/2005 | Kochamba et al. | 600/37 |
| 6,972,026 B1 * | 12/2005 | Caldwell et al. | 606/213 |
| 6,988,984 B2 * | 1/2006 | Parsons et al. | 600/37 |
| 7,097,612 B2 * | 8/2006 | Bertolero et al. | 600/37 |
| 7,112,172 B2 | 9/2006 | Orban, III et al. | |
| 7,179,224 B2 * | 2/2007 | Willis | 600/205 |
| 7,226,409 B2 * | 6/2007 | Peng et al. | 600/37 |
| 7,235,049 B1 * | 6/2007 | Cohn | 600/235 |
| 7,294,103 B2 * | 11/2007 | Bertolero et al. | 600/207 |
| 7,297,153 B2 * | 11/2007 | Kieturakis et al. | 606/190 |
| 7,311,661 B2 * | 12/2007 | Heinrich | 600/206 |
| 7,311,719 B2 * | 12/2007 | Bonutti | 606/192 |
| 7,326,177 B2 * | 2/2008 | Williamson et al. | 600/201 |
| 7,338,441 B2 * | 3/2008 | Houser et al. | 600/206 |
| 7,485,090 B2 * | 2/2009 | Taylor | 600/37 |
| 7,497,824 B2 * | 3/2009 | Taylor | 600/37 |
| 7,736,306 B2 * | 6/2010 | Brustad et al. | 600/208 |
| 7,749,157 B2 * | 7/2010 | Bertolero | 600/116 |
| 7,749,415 B2 * | 7/2010 | Brustad et al. | 264/102 |
| 7,766,817 B2 * | 8/2010 | Peng et al. | 600/37 |
| 7,766,823 B2 * | 8/2010 | Moll et al. | 600/192 |
| 7,837,612 B2 * | 11/2010 | Gill et al. | 600/37 |
| 7,850,600 B1 * | 12/2010 | Piskun | 600/114 |
| 7,878,974 B2 * | 2/2011 | Brustad et al. | 600/208 |
| 7,931,579 B2 * | 4/2011 | Bertolero et al. | 600/37 |
| 8,092,378 B2 * | 1/2012 | Roth et al. | 600/206 |
| 8,251,900 B2 * | 8/2012 | Ortiz et al. | 600/208 |
| 8,282,545 B1 * | 10/2012 | Bodenstein | 600/206 |
| 8,317,695 B2 * | 11/2012 | Spence et al. | 600/235 |
| 8,382,654 B2 * | 2/2013 | Taylor | 600/37 |
| 2002/0069884 A1 * | 6/2002 | Boyd et al. | 128/898 |
| 2002/0074004 A1 * | 6/2002 | Boyd et al. | 128/898 |
| 2002/0082470 A1 * | 6/2002 | DeVries et al. | 600/37 |
| 2002/0095067 A1 | 7/2002 | Guenst et al. | |
| 2002/0099268 A1 * | 7/2002 | Paul et al. | 600/201 |
| 2002/0099269 A1 * | 7/2002 | Martin et al. | 600/201 |
| 2003/0073883 A1 * | 4/2003 | Stiles | 600/205 |
| 2003/0120205 A1 * | 6/2003 | Donaldson | 604/93.01 |
| 2004/0097792 A1 * | 5/2004 | Moll et al. | 600/201 |
| 2004/0138533 A1 * | 7/2004 | Spence et al. | 600/201 |
| 2005/0159650 A1 * | 7/2005 | Raymond et al. | 600/201 |
| 2005/0171403 A1 * | 8/2005 | Paolitto et al. | 600/205 |
| 2005/0209510 A1 * | 9/2005 | Bonadio et al. | 600/208 |
| 2006/0041194 A1 * | 2/2006 | Sorochkin et al. | 600/201 |
| 2006/0212114 A1 * | 9/2006 | Menicanti et al. | 623/2.36 |
| 2006/0247500 A1 * | 11/2006 | Voegele et al. | 600/208 |
| 2007/0088203 A1 * | 4/2007 | Lau | 600/205 |
| 2007/0232865 A1 | 10/2007 | Efinger et al. | |
| 2008/0091079 A1 * | 4/2008 | Roth et al. | 600/205 |
| 2008/0108876 A1 * | 5/2008 | Houser et al. | 600/206 |
| 2009/0062872 A1 * | 3/2009 | Chin et al. | 606/86 R |
| 2009/0082633 A1 * | 3/2009 | Kathrani et al. | 600/207 |
| 2009/0082634 A1 * | 3/2009 | Kathrani et al. | 600/207 |
| 2009/0118587 A1 * | 5/2009 | Voegele et al. | 600/206 |
| 2009/0143750 A1 * | 6/2009 | Falahee | 604/275 |
| 2009/0287060 A1 * | 11/2009 | Pell et al. | 600/201 |
| 2009/0326518 A1 * | 12/2009 | Rabin | 606/1 |
| 2010/0174149 A1 * | 7/2010 | Moll et al. | 600/203 |
| 2010/0228090 A1 * | 9/2010 | Weisenburgh et al. | 600/201 |
| 2010/0228094 A1 * | 9/2010 | Ortiz et al. | 600/205 |
| 2010/0256523 A1 * | 10/2010 | Uznanski et al. | 600/565 |
| 2010/0261972 A1 * | 10/2010 | Widenhouse et al. | 600/206 |
| 2010/0312061 A1 * | 12/2010 | Hess et al. | 600/201 |
| 2011/0054260 A1 * | 3/2011 | Albrecht et al. | 600/208 |
| 2011/0071361 A1 * | 3/2011 | Mollenauer et al. | 600/207 |
| 2011/0112372 A1 * | 5/2011 | Hajarian et al. | 600/205 |
| 2011/0112373 A1 * | 5/2011 | Ainsworth et al. | 600/207 |
| 2011/0112374 A1 * | 5/2011 | Brustad et al. | 600/208 |
| 2011/0306842 A9 * | 12/2011 | Voegele et al. | 600/206 |
| 2012/0203069 A1 * | 8/2012 | Hannaford et al. | 600/201 |
| 2013/0030252 A1 * | 1/2013 | Kaul | 600/204 |
| 2013/0030253 A1 * | 1/2013 | Titus | 600/207 |
| 2013/0109924 A1 * | 5/2013 | Gan | 600/205 |

FOREIGN PATENT DOCUMENTS

| | | |
|---|---|---|
| WO | 00/74574 A1 | 12/2000 |
| WO | 2007/127818 A2 | 11/2007 |
| WO | 2009/023136 A2 | 2/2009 |

OTHER PUBLICATIONS

Gentilli, S., et al., "Laparoscopic splenectomy: How to make it easier using an innovative atraumatic suction grasper", Surgical Endoscopy, 1998, vol. 12: pp. 1345-1347, Springer-Verlag New York Inc.

Vonck, D. et al., "Vacuum grasping as a manipulation technique for minimally invasive surgery", Surgical Endoscopy, 2010, vol. 24, pp. 2418-2423, Springer.

(56) References Cited

OTHER PUBLICATIONS

Shibao, K., et al., "Disk suspension method: a novel and safe technique for the retraction of the liver during laparoscopic surgery (with video)", Surgical Endoscopy, 2011, vol. 25, pp. 2733-2737, Springer.
Vonck, D., et al., "Grasping soft tissue by means of vacuum technique", Medical Engineering & Physics, 2011, Elsevier Ltd., www.elsevier.com/locate/medengphy, 7 pp.
Martin, J., et al., "Regulatory Pathway & Clinical Landscape, Project Impala", ingeneus—Accredited Medical Devices From Idea to Practice, Aug. 10, 2012, 17 pp.

* cited by examiner

FIG. 1A (ii)

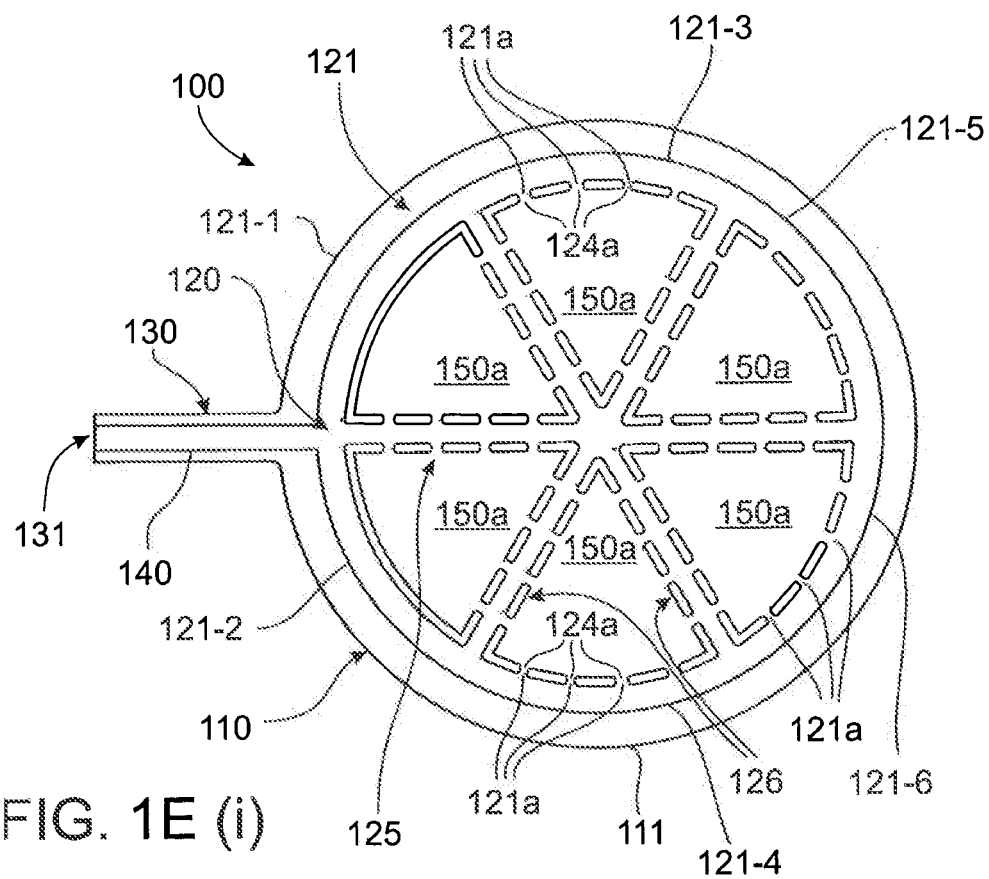
FIG. 1E (i)
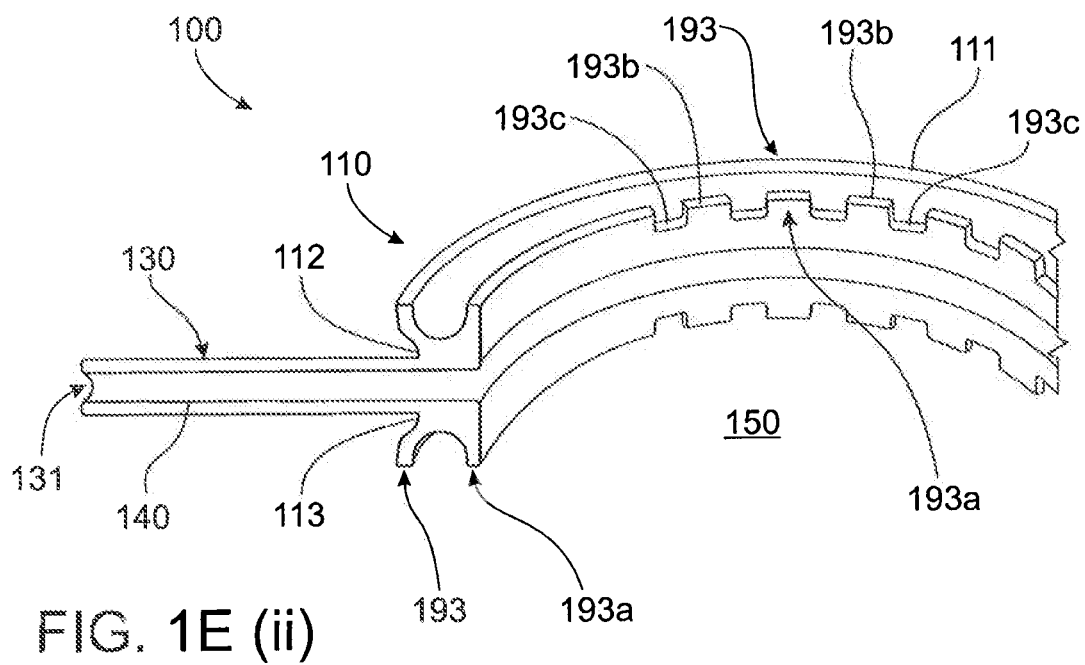
FIG. 1E (ii)

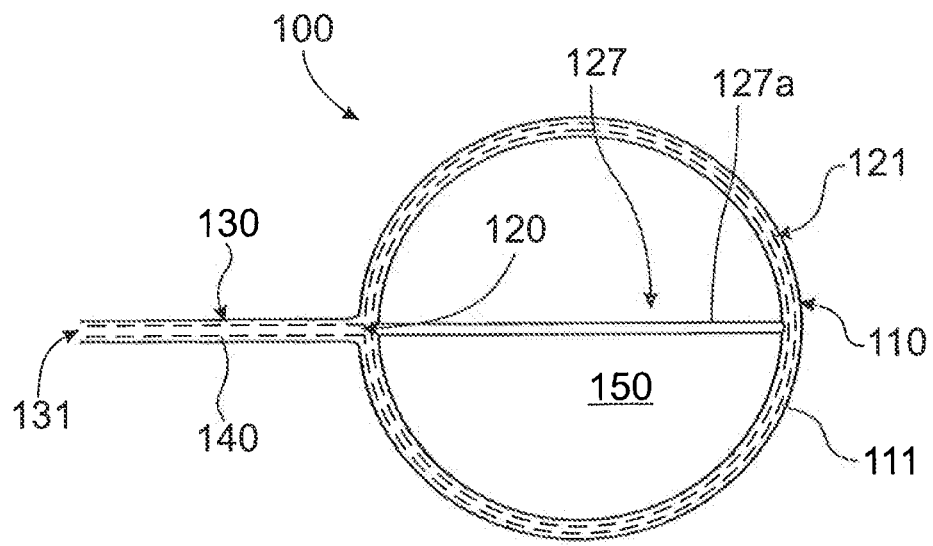
FIG. 1F(i)
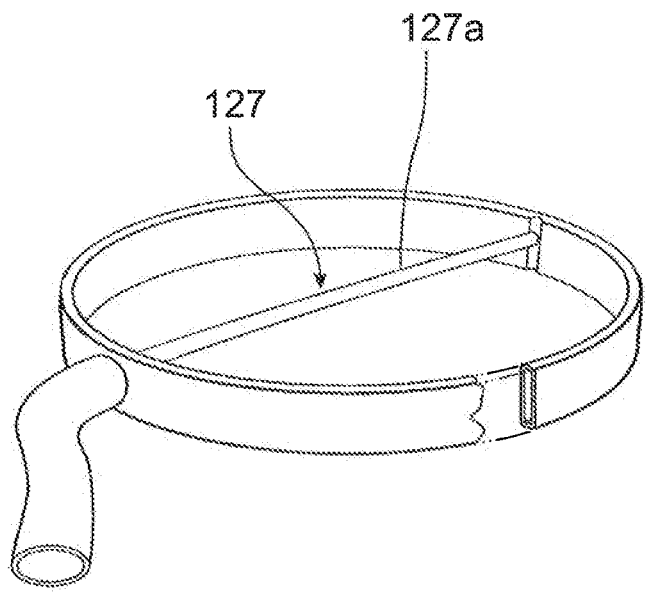
FIG. 1F(ii)

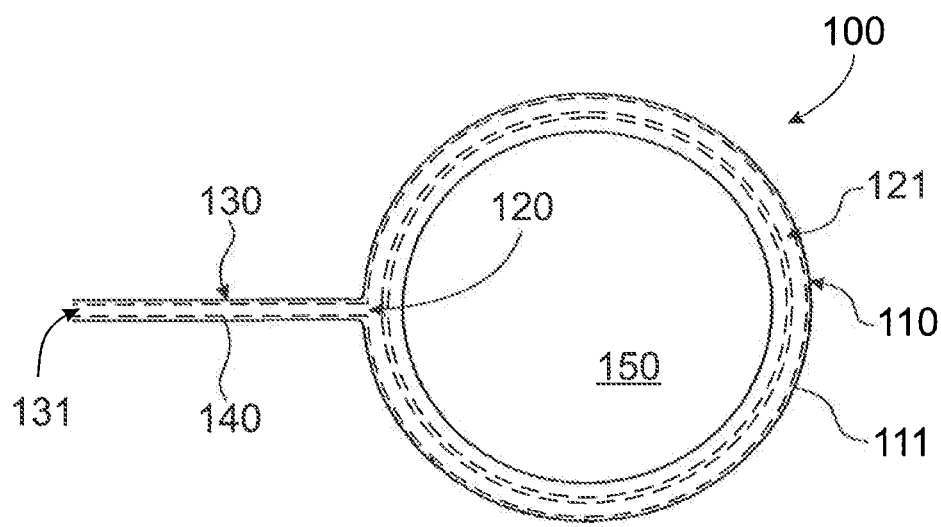
FIG. 1G (i)
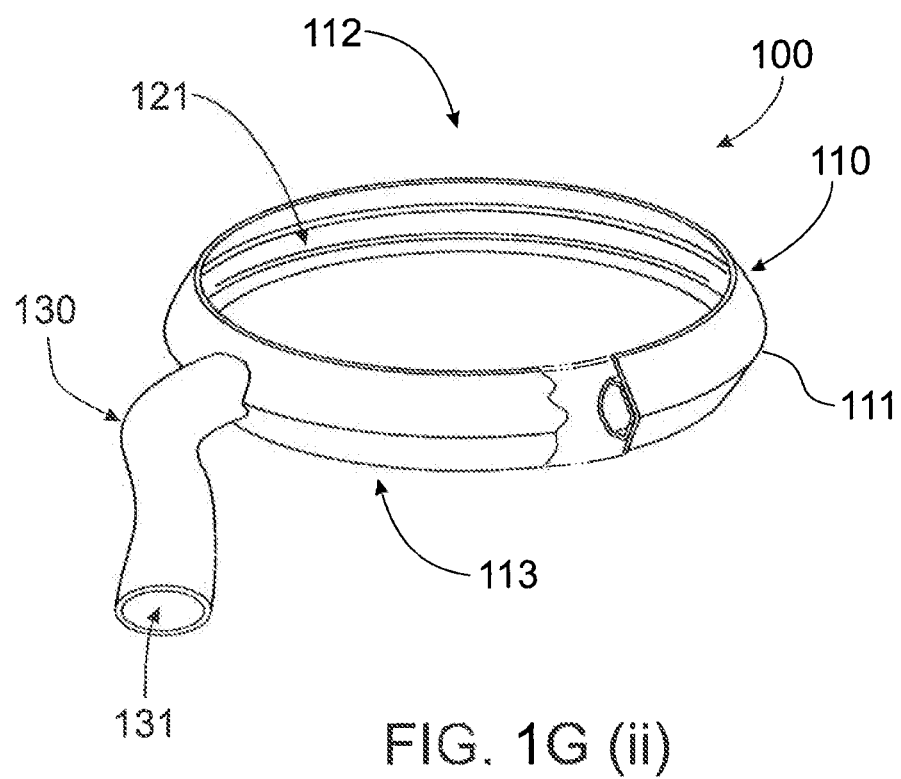
FIG. 1G (ii)

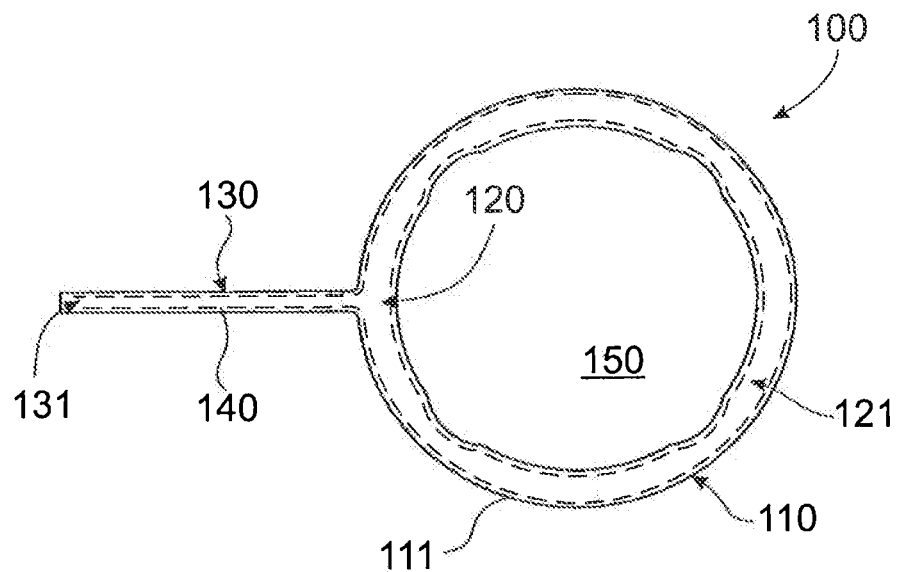
FIG. 1H (i)
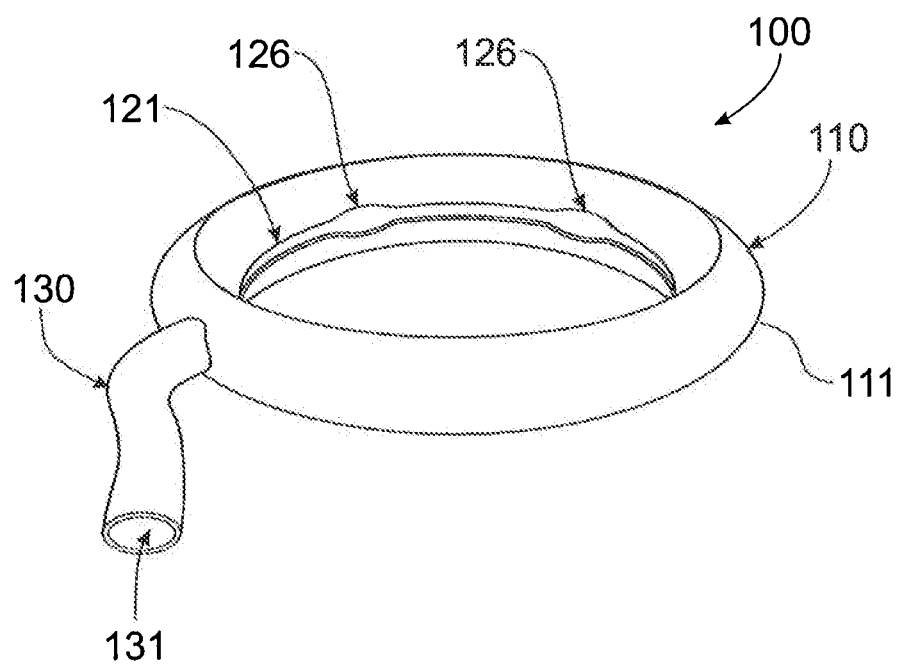
FIG. 1H (ii)

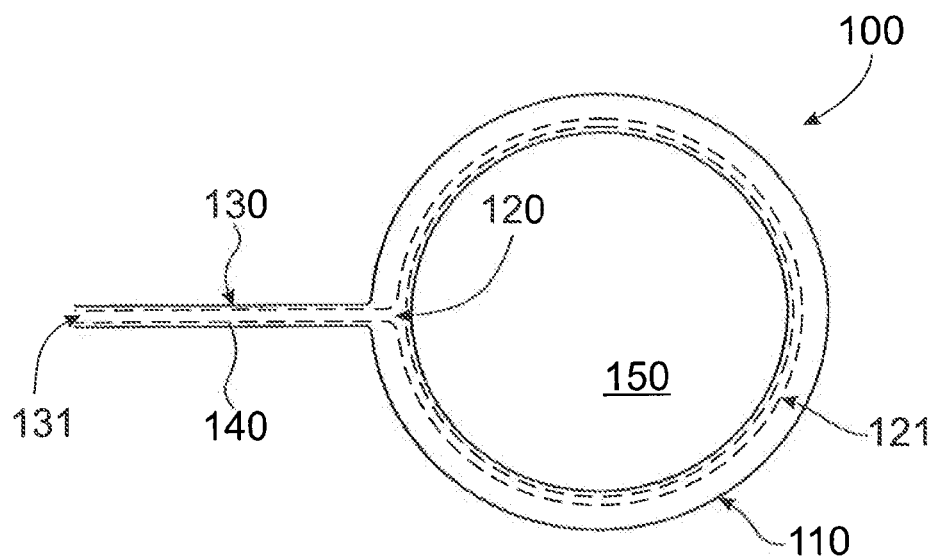
FIG. 1I (i)
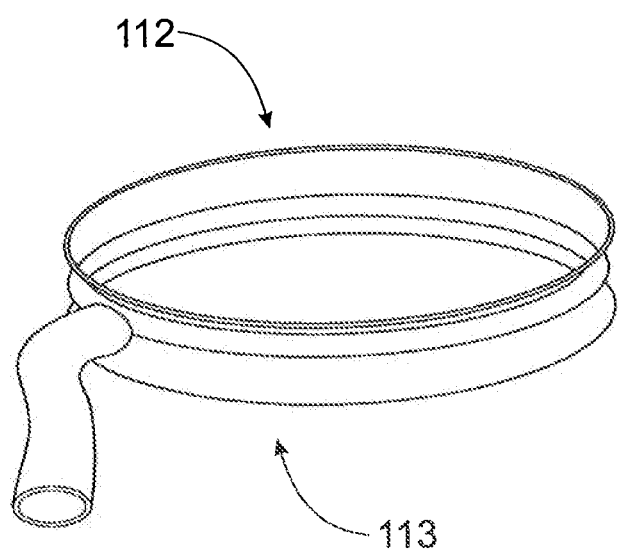
FIG. 1I (ii)

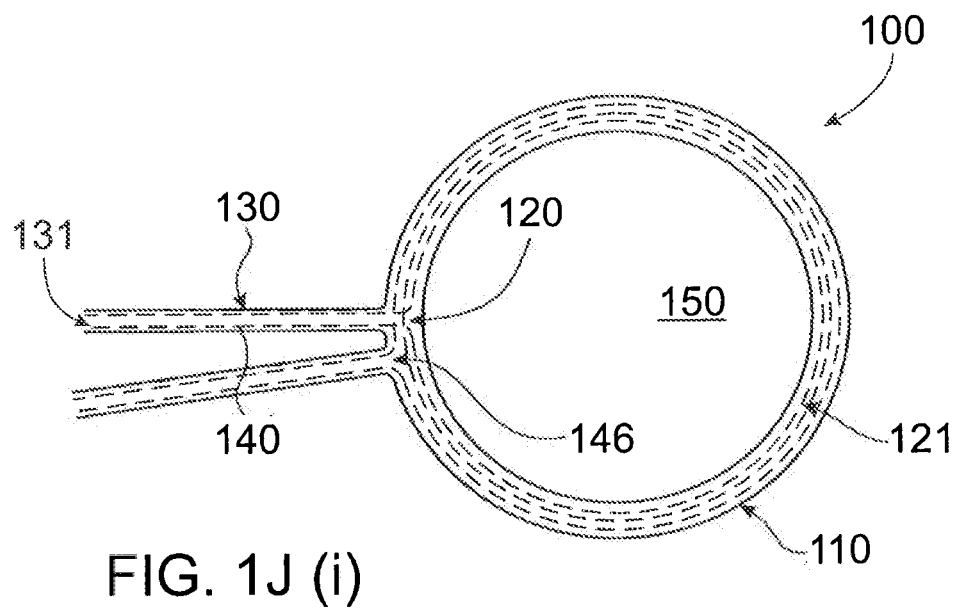
FIG. 1J (i)
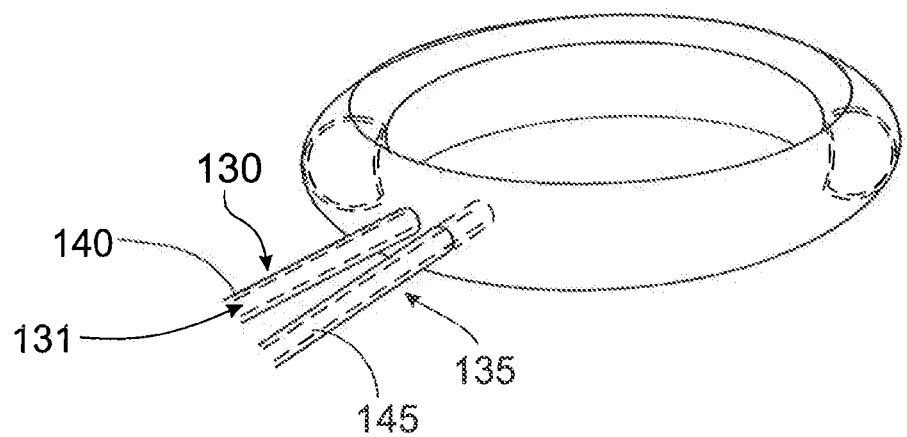
FIG. 1J (ii)

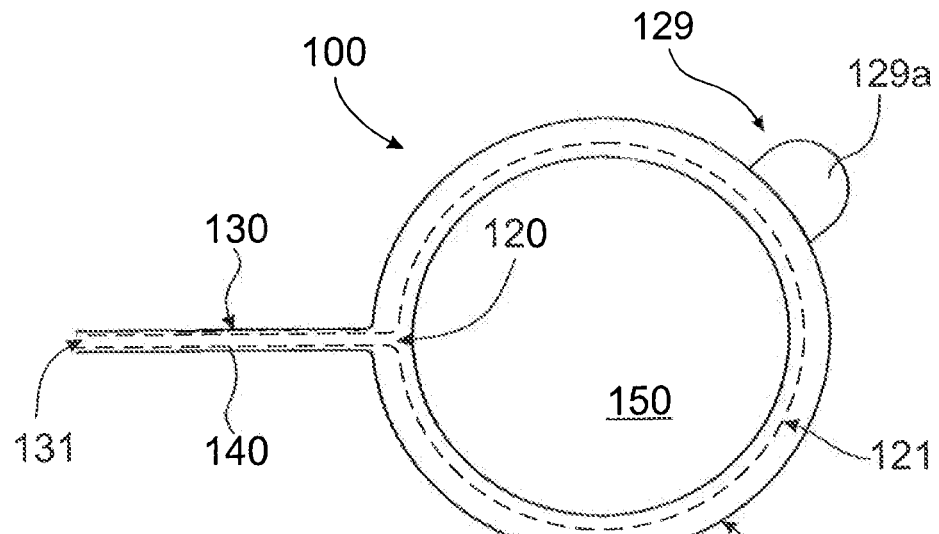
FIG. 1K
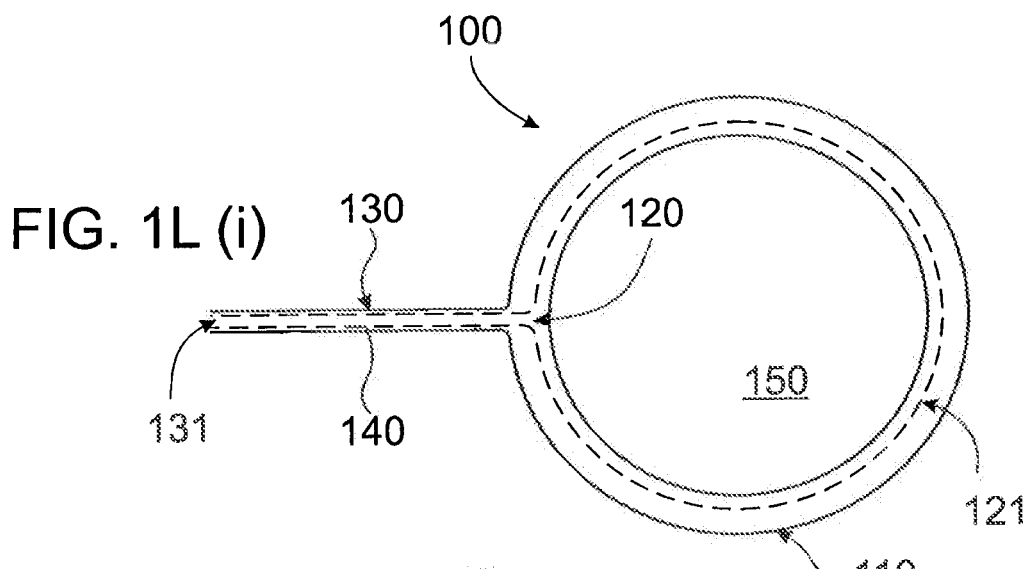
FIG. 1L (i)
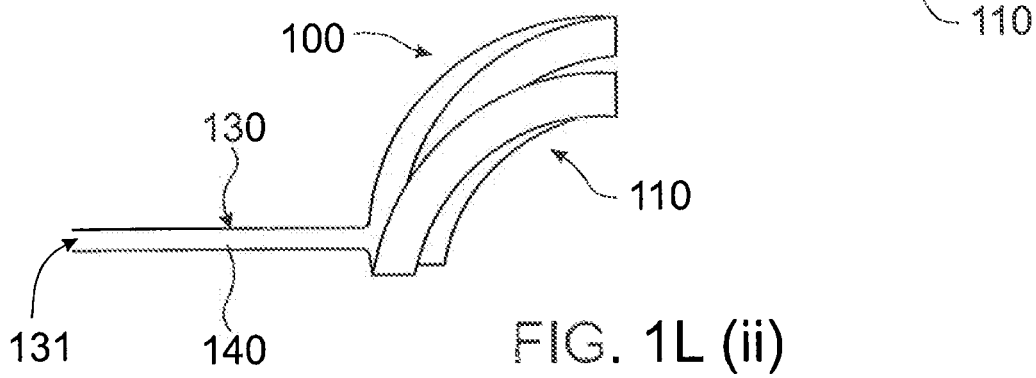
FIG. 1L (ii)

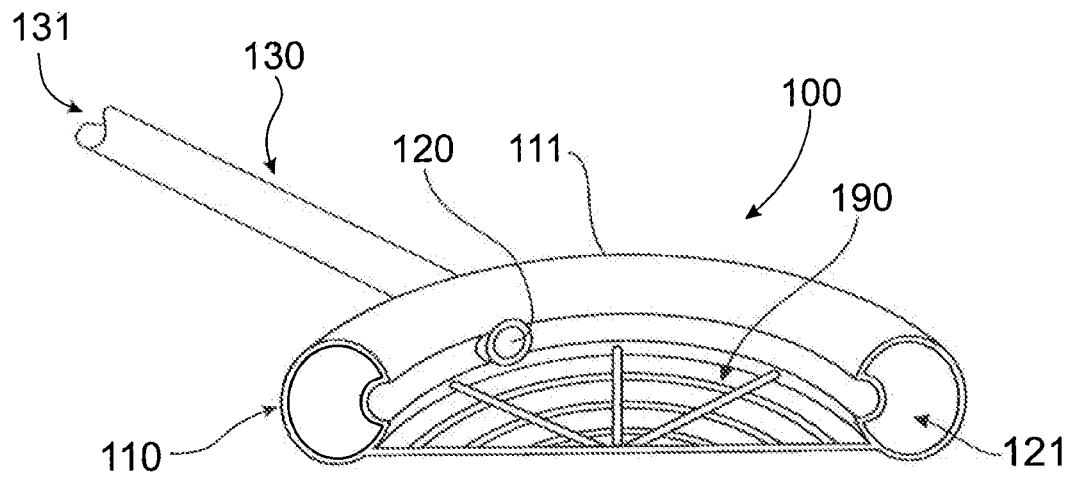
FIG. 1M (i)
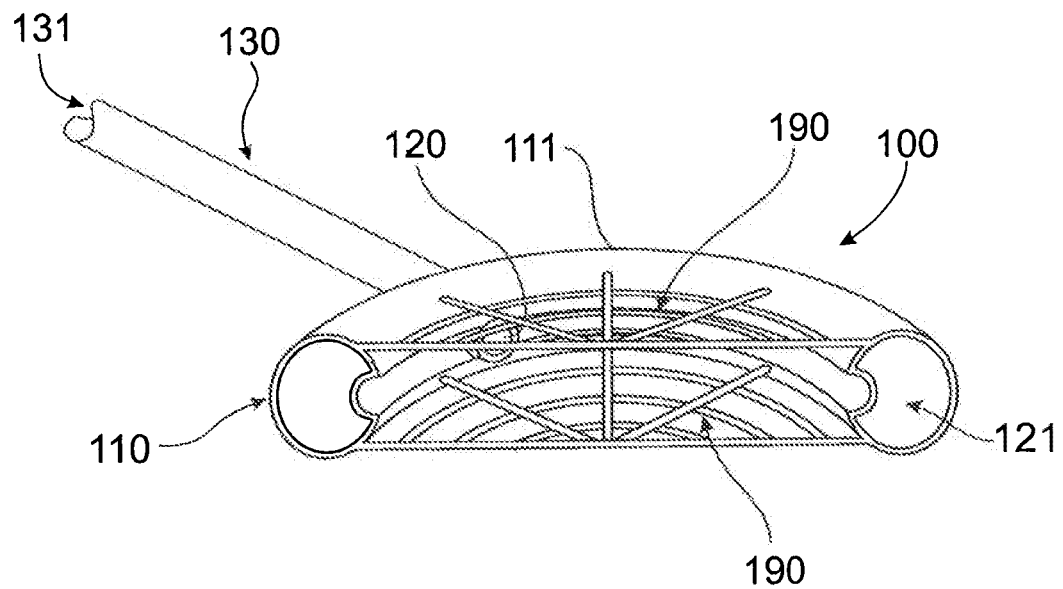
FIG. 1M (ii)

SUCTION RETRACTOR

FIELD OF THE INVENTION

The present invention relates to a suction retractor, method of surgery using a suction retractor, method of manufacturing a suction retractor and a kit comprising a suction retractor. In particular, but not exclusively, the present invention relates to a suction retractor that comprises a flexible continuous dam defining one or more inlet into an interior of the dam through which suction can be applied.

BACKGROUND TO THE INVENTION

Surgical procedures routinely require use of mechanical retractors to move a body part, tissue and/or an organ during the course of the surgery. These mechanical retractions require considerable skill to avoid causing trauma. Additionally, surgery is often carried out in a confined space that can become cluttered with such retractors.

The difficulty of using conventional mechanical retractors can be illustrated by briefly examining upper gastrointestinal surgery. Traditionally operating on abdominal organs required a "laparotomy" which is a large incision through the abdominal wall. One of the major advances in abdominal surgery over the last two decades has been laparoscopic surgery, which advantageously requires minimal access and thereby avoids the extent of trauma and scarring associated with a large incision. Laparoscopic surgery may be carried out by passing ports through multiple small incisions, or using Single Incision Laparoscopic Surgery (SILS) which utilizes only a single incision and single port. Advocates of SILS expound the advantages of reduced pain, trauma and scarring. Achieving adequate tissue retraction in SILS has proven to be a significant technical hurdle, as retractors that utilise the SILS port limit access of other instruments through that port. Suture techniques of retraction are time consuming and traumatic, whilst inserting a retractor through a separate port is not truly Single Incision Laparoscopic Surgery.

Accordingly there is a clear need for alternative retractors.

OBJECT OF THE INVENTION

It is an object of this invention to overcome and/or alleviate one or more of the above disadvantages of the prior art and/or provide the consumer with a useful or commercial choice.

It is a preferred object to provide a retractor that uses suction to retract one or more body part, tissue, organ or part thereof.

Further objects will be evident from the following description.

SUMMARY OF THE INVENTION

The present invention is broadly directed to providing a suction retractor as well as a method of surgery using a suction retractor, a method of making a suction retractor and a kit comprising a suction retractor. The present inventor has provided a novel and inventive retractor that simplifies many surgical procedures and can reduce the trauma and scarring consequent with surgical procedures such as, upper gastrointestinal surgery.

The simplification of many surgical methods that is preferably achieved by the suction retractor and methods of the invention is of significant advantage. Some of these advantages are safety related through a reduction in the risk of surgical error and promotion of the uptake of less traumatic surgical methods. The present invention is also of significant advantage commercially because the suction retractor may be disposable thereby eliminating the cost and effort required with disinfecting and cleaning.

In a first aspect, although it need not be the only, or indeed the broadest aspect, the invention resides in a suction retractor comprising:

a flexible continuous dam which forms a closed loop of any shape and which defines one or more inlet, the one or more inlet opening into an interior of the closed loop, so that suction can be applied through the one or more inlet and into an interior of the continuous dam.

The suction retractor may also comprise a suction tube defining a suction channel, the suction tube attached to or attachable to the continuous dam and when attached the suction channel continuous with the one or more inlet.

In a second aspect the invention resides in a method of retracting one or more body part, tissue, organ or part thereof using the retractor of the first aspect.

In a third aspect the invention resides in a method of retracting one or more body part, tissue, organ or part thereof including:

applying suction through a retractor, the retractor comprising one or more inlet defined in a flexible continuous dam, the continuous dam forming a closed loop of any shape and the one or more inlet opening into an interior of the closed loop, to thereby form a seal to the one or more body part, tissue, organ or part thereof and to allow retraction of the one or more body part, tissue, organ or part thereof.

The method of the third aspect may also include the step of applying suction through a suction tube attached to the continuous dam wherein the suction tube defines a suction channel continuous with the one or more inlet.

In a fourth aspect the invention resides in a method of manufacturing a suction retractor including:

forming a flexible continuous dam which forms a closed loop of any shape and which defines one or more inlet opening into an interior of the closed loop to thereby manufacture the suction retractor.

The method of the fourth aspect may also include forming or attaching a suction tube defining a suction channel so that the suction channel and one or more inlet are continuous.

In a fifth aspect the invention resides in a system for retracting a body part, tissue, organ and/or part thereof comprising:

a flexible continuous dam forming a closed loop of any shape and defining one or more inlet through which suction can be applied, the one or more inlet opening into an interior of the closed loop; and a suction tube defining a suction channel, the suction tube attached to or attachable to the continuous dam wherein when attached the suction channel is continuous with the one or more inlet.

The system according to the fifth aspect may also comprise an apparatus for applying suction through the suction tube and the one or more inlet.

In a sixth aspect the invention resides in a kit for retracting a body part, tissue, organ and/or part thereof comprising:

a flexible continuous dam forming a closed loop of any shape and defining one or more inlet through which suction can be applied, the one or more inlet opening into an interior of the closed loop; and a suction tube defining a suction channel, the suction tube attached to or attachable to the continuous dam wherein when attached the suction channel is continuous with the one or more inlet.

The kit according to the sixth aspect may also comprise an apparatus for applying suction through the suction tube and one or more inlet.

The kit according to the sixth aspect may also comprise instructions for use.

According to any of the above aspects the one or more inlet may extend into the interior area.

According to any of the above aspects the inlet may be recessed.

According to any of the above aspects the one or more inlet may open to a continuous channel extending throughout an interior of the closed loop.

According to any of the above aspects the continuous channel may comprise an open channel.

According to any of the above aspects the continuous channel may comprise a plurality of fenestrations.

According to any of the above aspects the continuous channel may be connected to a central rib.

The central rib may be connected to one or more radial rib.

The central rib may be fenestrated.

The one or more radial rib may be fenestrated.

According to any of the above aspects a guard may cover the one or more inlet.

According to any of the above aspects when the suction tube is attached to the continuous dam, the suction tube may be disposed laterally on the continuous dam.

When the suction tube is disposed laterally, the continuous dam and suction tube may be in a planar or substantially planar arrangement.

The planar or substantially planar arrangement may suitably allow conformational adaptation to the body part, tissue, organ or part thereof to which contact is made.

The continuous dam according to any of the above aspects may be planar or substantially planar.

According to any of the above aspects the flexibility of the continuous dam allows the dam to conformationally adapt to the body part, tissue, organ or part thereof to which contact is made.

The flexible continuous dam according to any of the above aspects may comprise a first compacted configuration for insertion and a second open configuration for retraction.

The flexible continuous dam according to any of the above aspects may transition from the compacted configuration to the open configuration by folding and unfolding, rolling and unrolling and/or collapsing and/or opening.

The transition may be manipulated by an opening mechanism operatively coupled to the retractor.

The retractor according to any of the above aspects may comprise one or more biasing member.

The biasing member may be a rod.

The rod may span the continuous dam.

The continuous dam according to any of the above aspects may be malleable.

The continuous dam according to any of the above aspects may have a shape memory.

The continuous dam according to any of the above aspects may be inflatable.

The inflatable continuous dam may comprise an inflation tube.

The continuous dam according to any of the above aspects may comprise opposed first and second walls.

The first and second walls may be partially separated by the continuous channel.

The first and/or second walls may inwardly angled.

The first and/or second walls may be outwardly angled.

The first and/or second walls may be tapered.

The first and/or second walls may comprise one or more reinforcement members.

The one or more reinforcement members may be collocated with the fenestrations in the continuous channel.

The continuous dam according to any of the above aspects may comprise a perforated membrane. The perforated membrane may comprise a central orifice. The perforated membrane may span at least a part of an area defined by dam walls.

The retractor according to any of the above aspects may comprise one or more projection that can be grasped and manipulated so as to secondarily retract or re-position the tissue, organ and/or part thereof.

According to any of the above aspects the continuous channel may comprise an opening to an area defined by the first and second dam walls.

According to any of the above aspects the first and/or second walls may comprise a convex outer surface.

The first and/or second walls may comprise a chamfer.

The first and/or second walls may comprise ridges of progressive or tiered heights.

The first and/or second wall may comprise one or more lip.

The one or more lip may be pliant.

The one or more lip may be rigid.

The one or more lip may be smooth.

The one or more lip may be turreted.

In a preferable embodiment the first and/or second wall may comprise a pliant outer lip.

In another preferable embodiment the first and/or second wall may comprise a rigid turreted inner lip.

In still another preferable embodiment the first and or second wall may comprise a pliant outer lip and a rigid turreted inner lip.

According to any of the above aspects the continuous channel may comprise a gutter or furrow.

According to any of the above aspects the gutter or furrow may comprise a C-shaped.

According to any of the above aspects the continuous channel may comprise a concave surface.

According to any of the above aspects the continuous dam may be circular, amorphous, triangular or shaped to conform to a body part, tissue, organ and/or part thereof to be retracted.

According to any of the above aspects a spacer may be comprised within the interior of the continuous dam.

The spacer may comprise a plurality of spacing ribs.

One or more spacing ribs may be radial or concentric.

One or more spacing ribs may be parallel.

One or more spacing ribs may be transverse.

The spacer may comprise a webbing.

The webbing may be positioned above and/or below the inlet or continuous channel.

According to any of the above aspects, suction applied into interior area is sufficient to effectively hold or secure one body part, tissue, organ or part thereof to another body part, tissue, organ or part thereof through retractor. This holding or securing preferably also actuates a retraction as the one body part, tissue, organ or part thereof is moved toward the other body part, tissue or organ.

Further features of the present invention will become apparent from the following detailed description.

In this specification, the terms "comprises", "comprising", "include" and "including" or similar terms are intended to mean a non-exclusive inclusion, such that a method, system or apparatus that comprises a list of elements does not include those elements solely, but may well include other elements not listed.

BRIEF DESCRIPTION OF THE DRAWINGS

In order that the present invention may be readily understood and put into practical effect, reference will now be made to the accompanying illustrations, wherein like reference numerals are used to refer to like elements, and wherein:

FIGS. 1A(ii), 1B, 1C, 1D, 1E(i), 1E(ii), 1F(i), 1F(ii), 1G(i), 1G(ii), 1H(i), 1H(ii), 1I(i), 1I(ii), 1J(i), 1J(ii), 1K, 1L(i), 1L(ii), 1M(i) and 1M(ii) are schematic diagrams of suction retractors according to other embodiments of the invention;

FIGS. 7A, 7B, 8, 9, 9A, 9B, 10, 11A, 11B, 12A, 12B, 12C and 12D show further embodiments of a suction retractor according to the invention.

DETAILED DESCRIPTION OF THE INVENTION

The invention relates, at least in part, to a retractor which uses suction to retract a body part, organ, tissue and/or part thereof. The present inventor has provided a novel and inventive retractor that simplifies many surgical methods. There are many advantages associated with the present invention including being compatible with true SILS as well as simplicity and rapidity of use. Additionally, the suction retractor, which advantageously may be used to retract any body part, tissue, organ or part thereof, is of further advantage because suction may be less traumatic than traditional mechanical manipulations. The suction retractor allows the necessary force to be more evenly distributed around the surface of the body part, tissue, organ and/or part thereof to be retracted and thereby minimizes the risk of trauma.

Further the suction retractor of the invention may be disposable and cheap to manufacture.

The present inventor has provided a novel retractor designed to achieve organ retraction in surgery, with particular application in single incision or conventional laparoscopic surgery. The novel retractor of the invention comprises an enclosed dam within which suction forces are applied. In one application the dam is placed in between the viscera (nominally liver and diaphragm), suction applied, and apposition of the viscera thereby maintained. It should be noted that, in the case of the liver and diaphragm, the dam is merely maintaining the normal anatomical relationship between these viscera, whereas normally the liver would drop down away from the diaphragm under influence of gravity at laparoscopic surgery.

The inventor does caution that the suction retractor of the invention may not be strong enough in cases where a large force must be applied to achieve the necessary retraction. These situations such as, where there are adhesions under a liver or very large organs, are in the minority and best dealt with using traditional mechanical retraction.

As used herein "flexible" means capable of bending. As will be elucidated below the flexibility of the retractor of the invention means the retractor can transition from a first compacted configuration to a second open configuration.

Figure 1A:
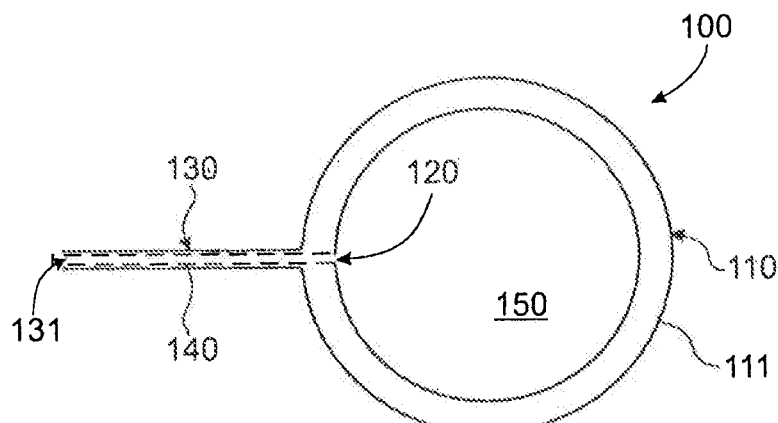
FIG. 1A(i) is a schematic diagram of a suction retractor according to a first embodiment of the invention.

FIG. 1A(i) shows one embodiment of the suction retractor 100 according to the invention. Suction retractor 100 comprises a continuous dam 110 that defines an inlet 120 through which suction is applied from suction tube 130. Inlet 120 comprises an opening or orifice into interior area 150 from suction channel 140 comprised in suction tube 130.

As will be explained below a guard 191 may partially cover the one or more inlet 120 so that suction does not draw matter such as, a body part, organ or part thereof to be retracted, into one or more inlet 120.

In another embodiment inlet 120 may be recessed into dam 110 to prevent matter being draw into inlet 120.

FIG. 1A(ii) shows another embodiment of the suction retractor 100 in which inlet 120 opens to a continuous channel 121 through which suction can be applied. The structure of continuous channel 121 is discussed in detail below with reference to FIG. 2.

As shown in FIGS. 1A(i) and 1A(ii), continuous dam 110 forms a loop 111 which surrounds and defines an interior area 150. Using retractor 100 suction can be applied into interior area 150.

As will be understood the suction applied into interior area 150 is sufficient to effectively hold or secure one body part, tissue, organ or part thereof to another body part, tissue, organ or part thereof through retractor 100. This holding or securing preferably also actuates a retraction as the one body part, tissue, organ or part thereof is moved toward or held adjacent to the other body part, tissue or organ.

In the embodiment shown in FIG. 1A(i) inlet 120 does not extend into interior area 150. In other embodiments inlet 120 extends into interior area 150.

Suction retractor 100 may also comprise a flexible suction tube 130 that defines a suction channel 140. As shown in FIG. 1A(i) and FIG. 1A(ii) suction channel 140 is continuous with inlet 120 and continuous channel 121, respectively. Suction tube 130 also comprises proximal tube port 131 which may be attached to an apparatus for applying suction through suction channel 140.

In another embodiment suction tube 130 is removably attachable to continuous dam 110. This allows suction tube 130 to be removed and attached as required.

Figure 6A:
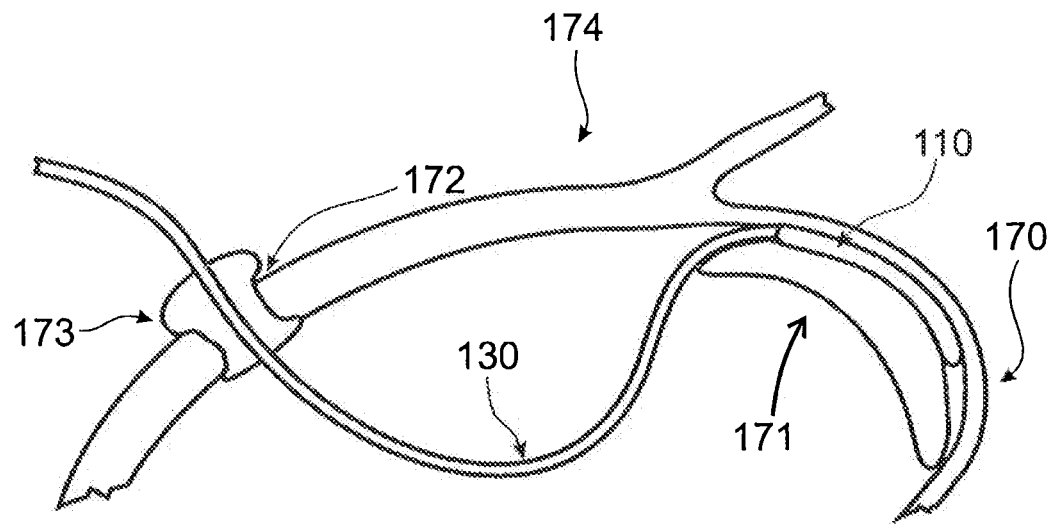
FIGS. 6A, 6B and 6C are schematic diagrams, showing cut-away views of the suction retractor according to the first embodiment in use.
Figure 6B:
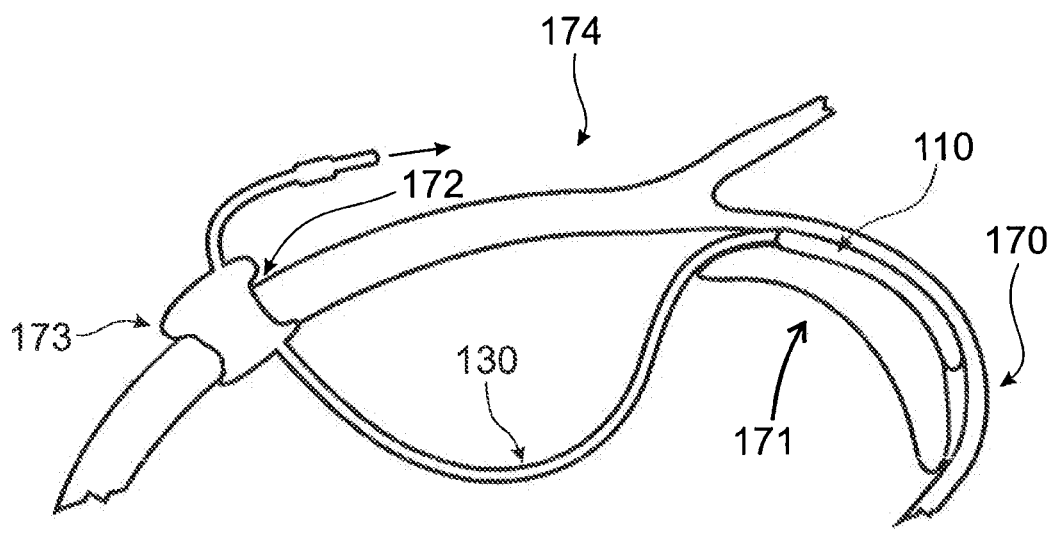
Figure 6C:
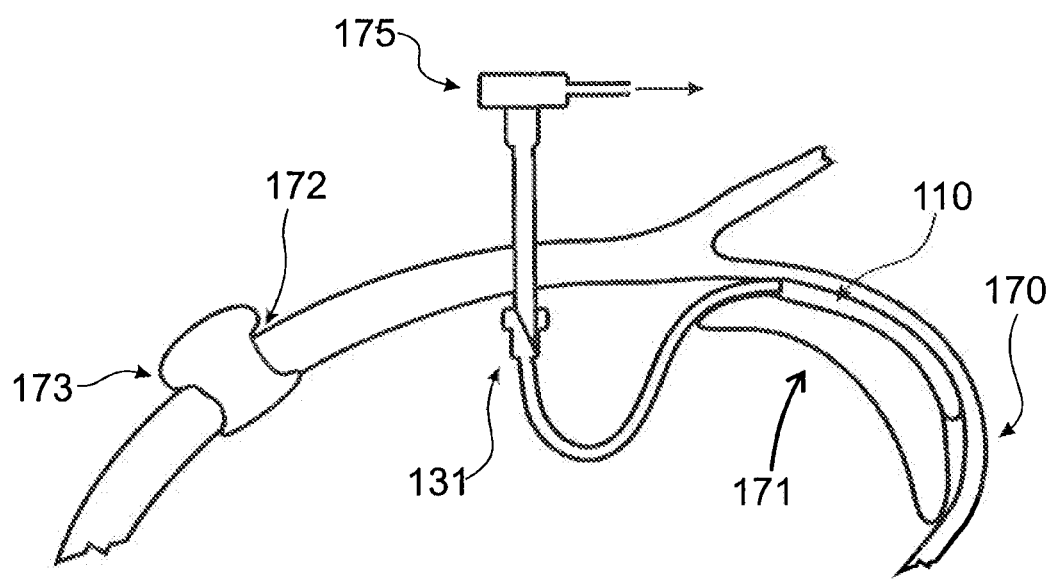

Continuous dam 110 is planar or substantially planar. As can be seen in FIGS. 6A-6C the planar or substantially planar shape allows continuous dam 110 to be positioned or sandwiched between two adjacent and/or abutting body parts, tissues, organs or parts thereof. The flexible and planar or substantially planar arrangement suitably allows conformational adaptation to the body part, tissue, organ or part thereof being retracted.

To enable positioning of continuous dam 110, suction tube 130 may be disposed laterally on continuous dam 110. This lateral arrangement results in retractor 100 having a planar or substantially planar shape as shown in the embodiments illustrated in FIGS. 1A(i), 1A(ii), 1B, 1C, 1D and 1E(i) and 1E(ii).

Figure 1B:
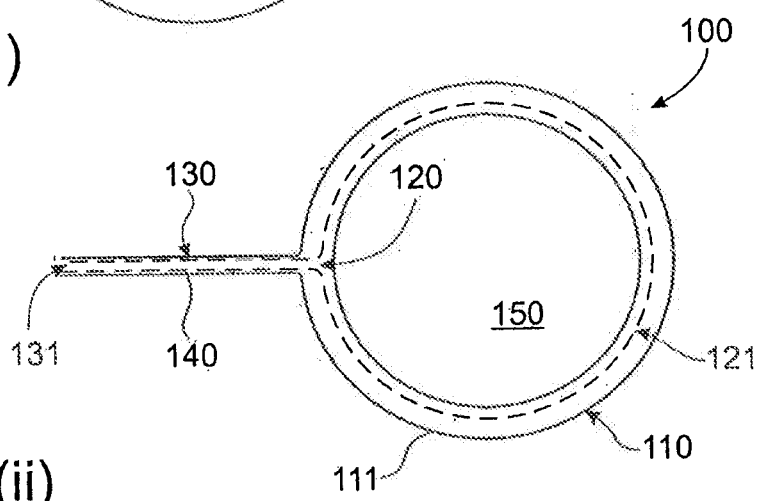
Figure 1B:
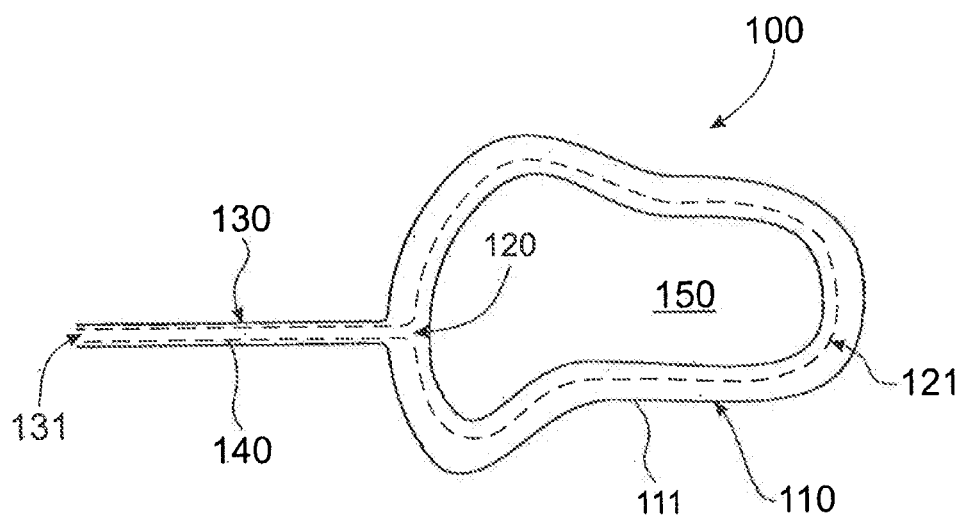
Figure 1C:
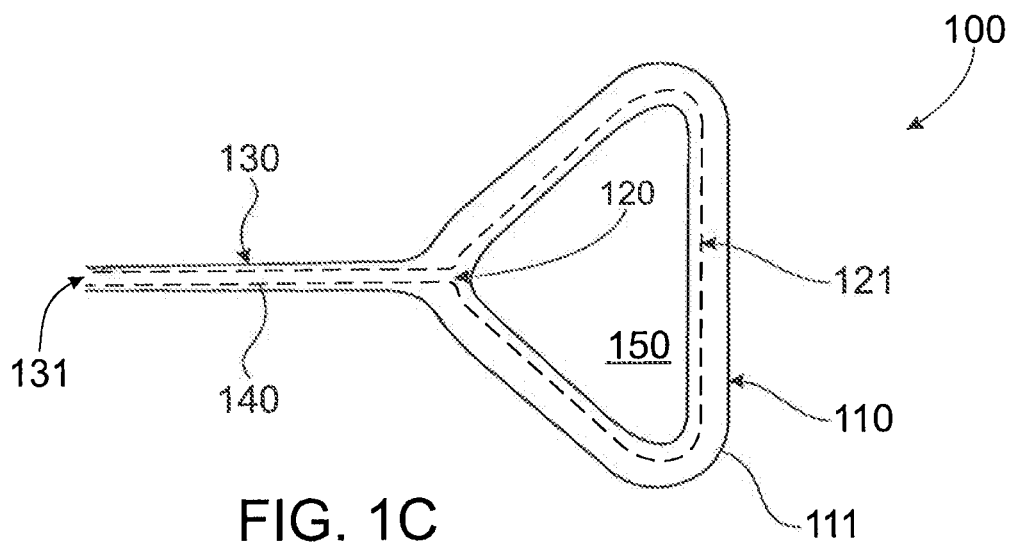

Dam 110 of retractor 100 shown in FIGS. 1A(i) and 1A(ii) is annular. Based on the teachings herein a skilled person is readily able to select other suitable shapes for dam 110. For example, FIGS. 1B and 1C show embodiments in which dam 110 is amorphous and triangular, respectively. Other suitable shapes for dam 110 include rectangular, square, pentagonal and hexagonal. Dam 110 may be shaped to conform to a particular body part, tissue, organ and/or part thereof to be retracted.

Figure 1D:
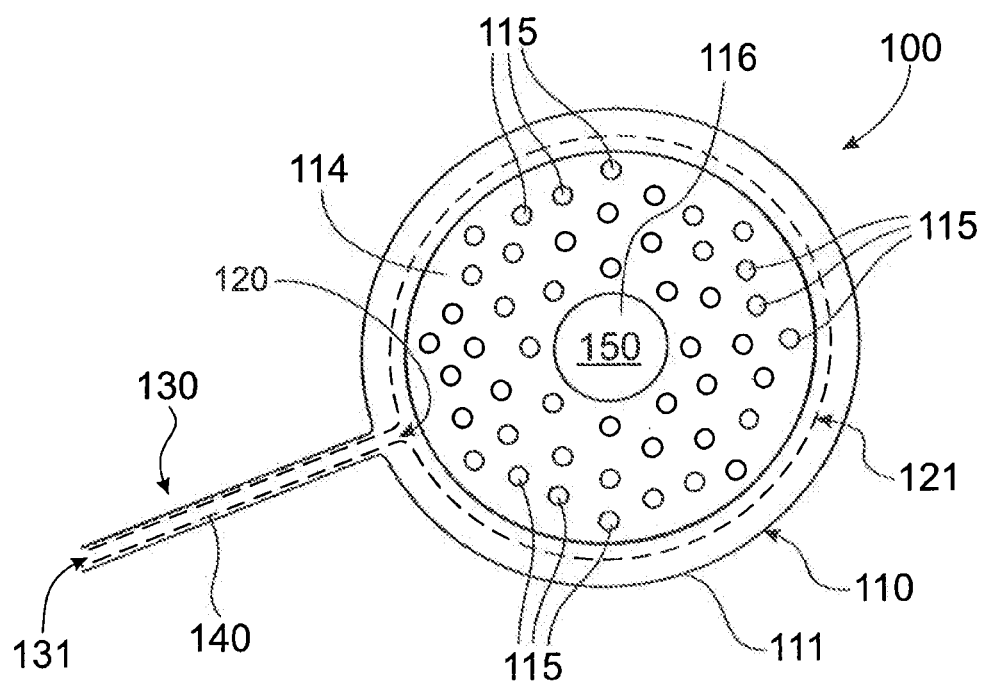

FIG. 1D shows another embodiment of retractor 100 comprising a membrane 114. Membrane 114 comprises multiple perforations 115 and defines a central orifice 116. To avoid cluttering FIG. 1D not all perforations 115 are labelled. The perforated membrane spans at least a part of the interior area 150 defined by walls 112, 113 (see FIG. 2 and further description below):

Perforated membrane 115 is preferably thinner than dam 110.

FIG. 1E(i) shows a top view of another embodiment of retractor 100. Retractor 100 shown in FIGS. 1E(i) and 1E(ii) comprises a fenestrated continuous channel 121. By fenestrated is meant a series of fenestrations or openings or windows 121a along the length or continuous channel 121. In other embodiments, for example those shown in FIGS. 1A(ii), 1B, 1C, 1D and FIG. 2, continuous channel 121 is open. In the embodiment shown in FIG. 1E, continuous channel 121 is connected to a central rib 125 which in turn is connected to one or more radial ribs 126. Both central rib 125 and the one or more radial ribs 126 are fenestrated to supply suction into interior area 150. Ribs 125, 126 divide the interior area 150 into sections 150a.

In the embodiment shown in FIGS. 1E(i) and 1E(ii) the proximal sections of continuous channel 121, that is, those sections 121-1 and 121-2 extending from inlet 120 to the first radial rib 126 are closed. The distal sections of continuous channel 121, that is, those central sections 121-3 and 121-4 extending between the radial ribs 126; and those end sections 121-5 and 121-6 extending between the radial ribs 126 and the central rib opposite inlet 120; comprise a fenestrated channel 121. In other embodiments the distal sections 121-3, 121-4, 121-5 and 121-6 are open comprising a gutter or furrow 122 and do not comprise fenestrations 121a. In still other embodiments the entire continuous channel 121 is fenestrated.

FIG. 1E(ii) shows a cut-away perspective view of retractor 100 shown in FIG. 1E(i) in which ribs 125, 126 are omitted. The cut-away view shows the first and second walls 112, 113 to comprise an outer lip 193 and an inner lip 193a. Outer lip 193 is pliant to conform to the body part, tissue or organ to be contacted and to which a seal is to be made. Inner lip 193 is more rigid and turreted to provide support for the dam 110 while gripping to the body part, tissue or organ to be contacted. The turreted lip 193a comprises a series of turrets or spaced apart teeth 193b which are separated by a series of valleys 193c.

As will be elucidated below with reference to FIGS. 7 and 9, a spacer 190 may be inserted into interior area 150 to assist in keeping parts on opposite sides of continuous dam 110 separated.

Spacer 190 may be of any suitable shape and material. The spacer 190 may comprise a foam material or a mesh material. Preferably spacer 190 is a mesh. As will be described below spacer 190 may comprise a plurality of radial or concentric spacing ribs 194, one or more parallel spacing ribs 195 and/or one or more transverse spacing rib 196.

FIGS. 1F(i) and 1F(ii) show top and perspective views, respectively of another embodiment of retractor 100 comprising biasing member 127. For sake of simplicity channel 121 has been omitted from FIG. 1F(ii). In the embodiment shown in FIGS. 1F(i) and 1F(ii) biasing member 127 is a rod 127a that spans continuous dam 110 and provides a bias from the compacted configuration to the open configuration. The bias imparts good spring back from the compacted configuration to the open configuration. The biasing member 127 may be operated by the opening mechanism. Based on the teaching herein a skilled person is readily able to select other suitable biasing members 127. In other embodiments retractor 100 comprises a plurality of biasing members.

FIGS. 1G(i) and 1G(ii) show top and perspective views, respectively of yet another embodiment of retractor 100 comprising inwardly-angled or V-shaped walls 112, 113 which angle inwardly towards interior area 150. Inwardly-angled walls 112, 113 improve the conformational fit with the body part, tissue or organ being contacted and may improve and/or strengthen the seal.

FIGS. 1H(i) and 1H(ii) show top and perspective views, respectively of a further embodiment in which retractor 100 comprises reinforcement members 126 positioned in channel 121. Reinforcement members 126 are substantially more rigid than continuous dam 110 and will maintain an open configuration under compressive force that would collapse channel 121. The reinforcement members may be co-located with the plurality of openings or fenestrations 124. The reinforcement members may prevent loss of suction if walls 112, 113 collapse.

The embodiment of retractor 100 illustrated in top and perspective views of FIGS. 1I(i) and 1F(ii), respectively, has walls 112, 113 which are outwardly angled, i.e. angled away from interior area 150, and which may create a suction-cup like effect to increase suction. Advantageously, by outwardly angling walls 112, 113 the surface area of contact is increased and the seal may be improved.

Accordingly, to any suitable embodiment of retractor 100, to improve the seal, walls 112, 113 may be tapered. The improved sealing effect of tapered walls 112, 113 will be particularly apparent with inwardly and outwardly angled walls 112, 113, like those embodiments shown in FIGS. 1G and 1I.

FIGS. 1J(i) and 1J(ii) show top and perspective views, respectively of an embodiment of retractor 100 which transitions to an open configuration by being inflated from its collapsed configuration. Inflation and deflation occurs through inflation tube 135 which defines inflation channel 145 and opens into inflation inlet 136 in dam 110. Inflatable retractor 100 would advantageously have good surface contact and conformation to a sealing surface. An inflatable retractor 100 would also provide a relatively soft contact surface to reduce or limit any damage to the body part, tissue, organ or part thereof contacted by inflatable retractor 100.

FIG. 1K shows an embodiment of retractor 100 which comprises a projection 129 that can be grasped and manipulated so as to secondarily retract or re-position the tissue, organ and/or part thereof. In the embodiment shown in FIG. 1K, projection 129 is a tab 129a extending from dam 110 and is located distal to suction tube 130. In other embodiments retractor 100 may comprise a plurality of projections 129 positioned at various locations on dam 110.

Figure 2:
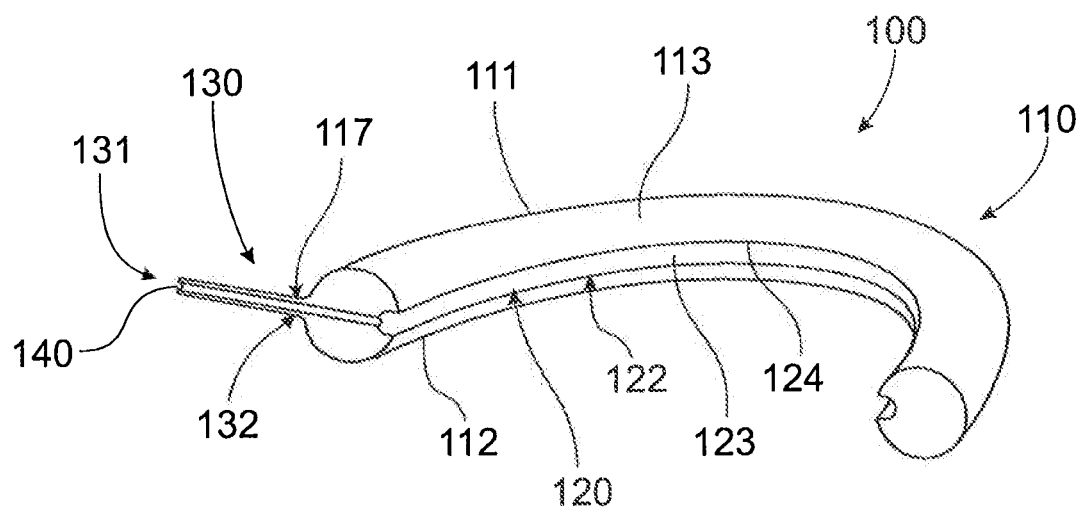
FIG. 2 is a schematic diagram showing a cut-away view of the suction retractor according to one embodiment of the invention.

As shown in FIG. 2 continuous dam 110 comprises first wall 112 and second wall 113 which are joined and opposed to each other. Walls 112 and 113 join at substantially the middle of dam 110, i.e. in embodiments of retractor 100 comprising central channel 121, walls 112, 113 are partially separated by continuous channel 121. In the embodiment of retractor 100 shown in FIG. 2 first and second walls 112, 113 comprise a hemi-spherical cross-section and comprise a curved or convex outer surface that does not have any edges and thereby minimizes the risk of retractor 100 causing any internal damage. Based on the teaching herein a skilled person is readily able to select alternative cross-sectional profiles for walls 112, 113. For example, walls 112, 113 may comprise a chamfer 180, see FIG. 7B or may comprise ridges of progressive or tiered height.

Additionally, as described above with reference to FIGS. 1E(i) and 1E(ii) and below with reference to FIGS. 11A and 11B, walls 112, 113 may comprise a lip 193 and or an inner lip 193a.

In other embodiments the outer surface of walls 112, 113 are not curved and instead are flat or planar. The flat surfaces may have edges or corners or may have tapered edges. Based on the teaching herein a skilled person is readily able to chose a suitable shape for walls 112, 113.

In the embodiment shown in FIG. 2, continuous channel 121 is a C-shaped gutter or furrow 122 that comprises a concave surface 123. In other embodiments channel 121 may have another shape such as, a V-shape. A skilled person is readily able to select an alternate shape for channel 121.

As shown in FIG. 2 to generate suction in interior area 150, retractor 100 comprises an opening 124 in continuous channel 121 which opens out to interior area 150. In the embodiment shown in FIG. 1A(ii) and FIG. 2 a single opening 124 runs the length of continuous channel 121. In the embodiment shown in FIGS. 1E(i) and 1E(ii) retractor 100 comprises a plurality fenestrations 121a which extend only part of the length of continuous channel 121. Each fenestration 121a has its own opening 124a. The plurality of fenestrations 121a and associated openings 124a may be spaced equidistantly and intermittently along the length of fenestrated continuous channel 121 so as to obtain an even suction.

Opening 124 allows suction applied through continuous channel 121 to form a seal between two internal structures which suction retractor 110 is sandwiched between. Once this seal has been formed the internal structures may be retracted.

In the embodiments shown in FIGS. 1D, 1E(i) and 1E(ii) the suction to the body part, tissue, organ or part thereof is applied through multiple perforations 115 and multiple openings 124a, respectively.

The continuous dam 110 shown in FIGS. 1A(i), 1A(ii) and 1D has a diameter of 50 mm, with a suitable range of 30-80 mm to allow for pediatric to "super-sized" patient applications. The continuous dam 110 shown in FIG. 1B has a longest span of 60 mm and a shortest span of 40 mm. The length of the sides of dam 110 shown in FIG. 1C is 50 mm.

Walls 112 and 113 have a thickness of 3 mm each, comprising a combined thickness of 6 mm. A suitable range for thickness of walls 112 and 113 is 3-6 mm.

Perforated membrane 114 has a thickness of 4 mm. A suitable range for thickness of perforated membrane 114 is 3-6 mm.

Perforations 115 have a diameter of 4 mm. A suitable range for the diameter of perforations 115 is 2-5 mm.

Orifice 116 has a diameter of 10 mm. A suitable range for the diameter of orifice 116 is 2 mm-30 mm.

Continuous channel 121 has a diameter of 2 mm. A suitable range for the diameter of continuous channel 121 is 1-3 mm.

Opening 124 has a width of 2 mm. A suitable range for opening 124 is 1-3 mm.

Suction tube 130 has a diameter of 5 mm and suction channel 140 has a diameter of 3 mm. Suitable ranges for the diameter of suction tube 130 and suction channel 140 are 4-7 and 3-5 mm, respectively.

Suction tube has a length of 50 cm. The length may be tailored to the particular surgical technique and is likely to be the in range of 10 cm-3 meters.

Based on the teachings herein a skilled person is readily able to select suitable values for the dimensions discussed above. It is also to be understood the dimensions included herein are indicative only and the invention is not so limited.

As mentioned above, in order to be inserted through a tract in laparoscopic surgery retractor 100 is preferably flexible and/or collapsible. As a result of this flexibility and/or collapsibility, retractor 100 may have a first compacted configuration for insertion and a second open configuration for contraction.

To transition between the compacted configuration and the open configuration retractor 100 may be folded and unfolded, rolled and unrolled and/or collapsed and released. Preferably the transition is reversible.

FIG. 1L(i) shows one embodiment of the retractor 100 in an open configuration and FIG. 1L(ii) shows the retractor of FIG. 1L(i) in a compacted configuration. The compacted configuration in FIG. 1L(ii) is a rolled configuration.

The transition may be accomplished manually or automatically by operatively coupling an opening mechanism (not shown) to retractor 100. The opening mechanism may act on the biasing member 127. From the teaching herein the skilled person is readily able to select a suitable opening mechanism.

In addition to being malleable retractor 100 may also have a shape memory. This shape memory allows the retractor to return to its original and intended shape after being compacted for example, to fit through a surgical port or to be positioned for retraction.

To achieve the desired level of malleability dam 100 is comprised of a suitable biocompatible medical grade synthetic material such as, soft and/or pliable silicones and/or plastics.

As will be discussed below the malleability enables retractor 100 to be folded into a compact size to allow insertion through a surgical port. The malleability also aids retractor 100 to adapt to the shape of the body part, tissue, organ and/or part thereof to be retracted. This feature of the invention advantageously improves the suction applied.

FIG. 1M(i) shows yet another embodiment of the retractor 100 of the invention in which spacer 190 is in the form of a webbing. In FIG. 1M(i) the webbing is located on one side, e.g. below, or in use an inferior surface, of continuous channel 121. In FIG. 1M(ii) the webbing is located on both sides, e.g. above and below, or in use an inferior surface and a superior surface, of continuous channel 121. The webbing, like other spacers 190, is useful in preventing matter from being drawn into inlet 120 or channel 121.

Retractor 100 may also be used in conventional surgical techniques. In these techniques there is no requirement for retractor 100 to be inserted through a surgical port and in such instances retractor 100 may have a size as large as required to retract the body part, tissue, organ and/or part thereof of interest.

Retractor 100 may be used to retract any body part, tissue, organ or part thereof. For example, retractor 100 may be used to retract either the left or right lobe of the liver during SILS, or any suitable body part, tissue, organ or part thereof.

As noted above, the invention also provides a method 200 of retracting one or more body part, tissue, organ or part thereof using retractor 100.

Figure 3A:
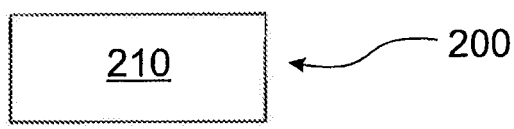
FIGS. 3A and 3B show embodiments of the method of surgery according to the invention.

According to one embodiment of method 200 shown in FIG. 3A in step 210 suction is applied through retractor 100 to form a seal to the one or more body part, tissue, organ or part thereof to thereby allow retraction of the one or more body part, tissue, organ or part thereof.

Before applying the suction the retractor 100 is positioned on or sandwiched between the body part, tissue, organ or part thereof to be retracted and another structure so that an adequate suction and vacuum can be created in order to facilitate retractions. The another structure may be another body part; tissue, organ and/or part thereof.

Figure 3B:
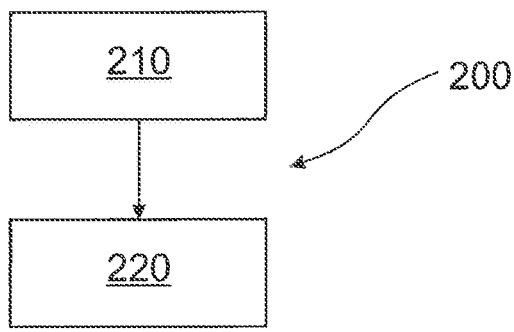

As shown in FIG. 3B, method 200 may also include the step 220 of applying suction through a suction tube 130 attached to the continuous dam 110 wherein the suction tube 130 defines a suction channel 140 continuous with the one or more inlet 120.

Figure 4A:
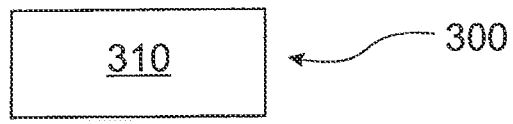
FIGS. 4A and 4B are schematic diagrams showing embodiments of the method of manufacturing a retractor according to the invention.

The invention also provides a method 300 of manufacturing a suction retractor 100. As shown in FIG. 4A, method 300 includes step 310 of forming a continuous dam 110 defining one or more inlet 120 to thereby manufacture the suction retractor 100. The continuous dam formed may also define continuous channel 121.

Figure 4B:
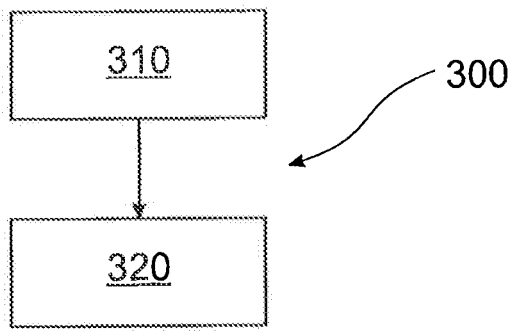

FIG. 4B shows another embodiment of method 300 including the further step 320 of forming or attaching a suction tube 130 defining a suction channel 140 so that the suction channel 140 and one or more inlet 120 are continuous.

Figure 5A:
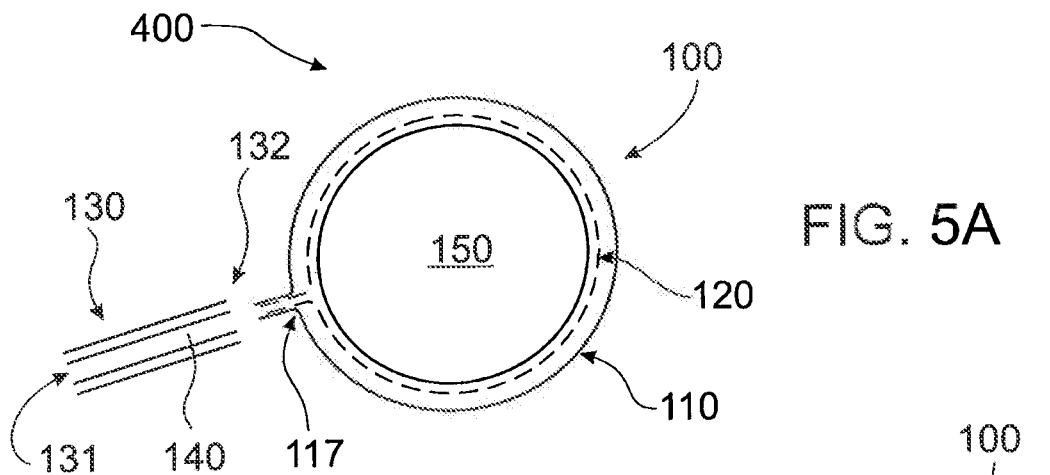
FIGS. 5A and 5B are schematic diagrams showing embodiments of the kit according to the invention.

FIG. 5A shows a kit 400 according to one embodiment of the invention which comprises a retractor 100 comprising continuous dam 110 and suction tube 130. Suction tube 130 may be attached to the continuous dam 110 by joining distal tube port 132 to dam port 117 so that suction channel 140 is continuous with inlet 120 and/or continuous channel 121.

Figure 5B:
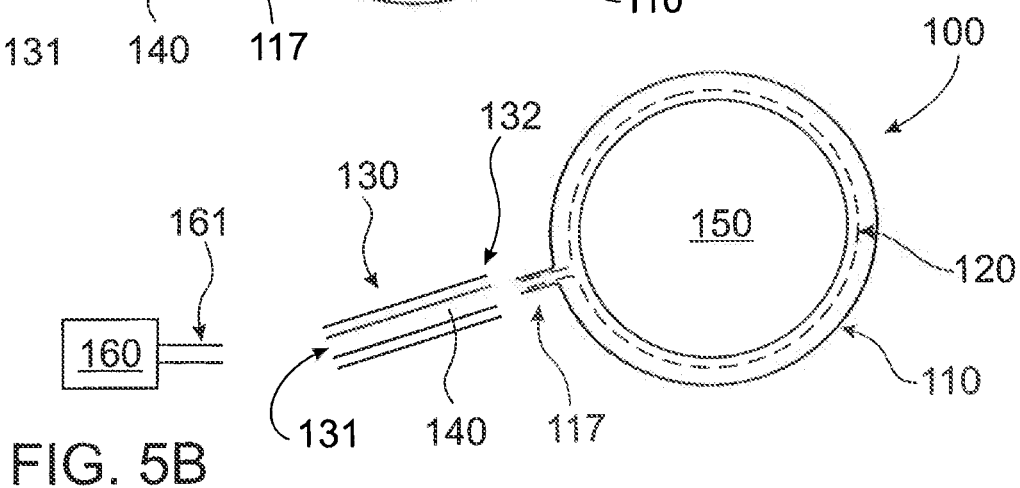

Another embodiment of a kit 400 according to the invention is shown in FIG. 5B which includes a suction apparatus 160 for applying suction through suction channel 140. Suction tube 130 is connected to apparatus 130 by joining proximal tube port 131 to suction apparatus port 161. Suction may be applied continuously or once a seal is attained, suction may be discontinued or applied only intermittently.

Suction apparatus 160 may be any conventional electronic suction device suitable for applying suction through a tube such as suction tube 130. In one embodiment suction apparatus 160 is a conventional 'wall suction' device through which variable suction pressure may be applied and adjusted by a lever. In another embodiment suction apparatus 160 may be an electronic suction device which is capable of monitoring and maintaining the degree of suction forces applied according to pre-determined settings. In yet another embodiment suction apparatus 160 may be a syringe which is withdrawn to apply suction and generate a seal using a lock or 3 way tap to maintain the suction forces, although in testing to date, this has been demonstrated to be ineffective in maintaining apposition of tissues.

Kit 400 may also comprise one or more laparascopic port 173 (see below) and/or instructions for use.

So that the invention may be readily understood and put into practical effect, the following non-limiting example is provided.

EXAMPLES

Example 1

LiVAC

Liver Vacuum Retraction

Although not limited thereto, the method of the invention will be further explained with reference to retraction of the liver to expose the organs beneath it during laparoscopic surgery. Retraction of the liver upwards is required in operations performed on the stomach or gallbladder. The retraction is necessary in order to access these organs. When used with the novel suction retractor 100 of the invention this technique is called LiVAC or Liver Vacuum Retraction.

Laparascopic surgery and open surgery require the application of force against the under-surface of the liver to lift it upwards. In laparoscopic surgery a dedicated tract or port is created for the insertion of the retractor and maintenance of the retraction. The retractor 100 and method 200 of the invention provide a means of retraction of the liver using suction between the upper (superior) surface of the liver, and the diaphragm.

As shown in FIG. 6A dam 110 may be positioned between diaphragm 170 and liver 171 and then suction applied through tube 130 so that the liver 171 and diaphragm 170 are held together in apposition and thereby retracted. The lateral attachments of the left lobe of liver to the diaphragm may be divided to reduce counter forces against the suction retraction.

In the embodiment shown in FIG. 6A dam 110 is inserted through laparoscopic port 173 which is positioned in surgical incision 172 cut in a patient's abdomen 174. Dam 100 is compacted and inserted through port 173 or through incision 172, with the tubing then brought back through a channel or connection in port 173. Tube 130 is also partially inserted through port 173.

Advantageously, suction retractor 100 is not only compatible with Single Incision Laparoscopic Surgery (SILS) techniques, but it greatly simplifies SILS. As shown in FIG. 6A, suction tube 130 is suitably narrow so as to enable it to pass through port 173 while still leaving a majority of the annulus of port 173 vacant to receive other laparoscopic instruments. In this way retractor 100 does not exert competing forces against other laparoscopic instruments also inserted through port 173.

FIG. 6B shows an embodiment in which suction tube 130 is integral with surgical port 173.

FIG. 6C shows that the retractor 100 of the invention is also compatible with a modified SILS technique in which in addition to port 173 a hollow needle or trochar 175 is inserted through the patient's abdomen 174. The hollow needle or trochar may be attached to suction tube 130 through proximal port 131.

In this modified SILS technique a shorter length of suction tubing 130 is required within the abdomen with only the addition of a tiny incision for accommodating the needle or trochar 175.

Retractor 100 may be used to retract either the left or right lobes of the liver.

Example 2

Acetal Prototype

Figure 7A:
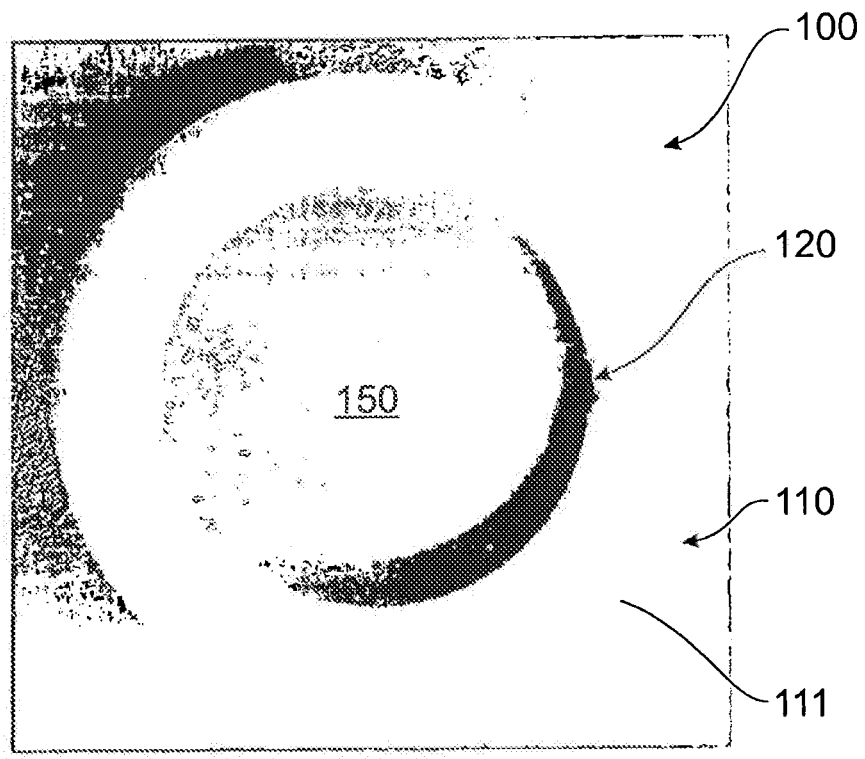
Figure 9A:
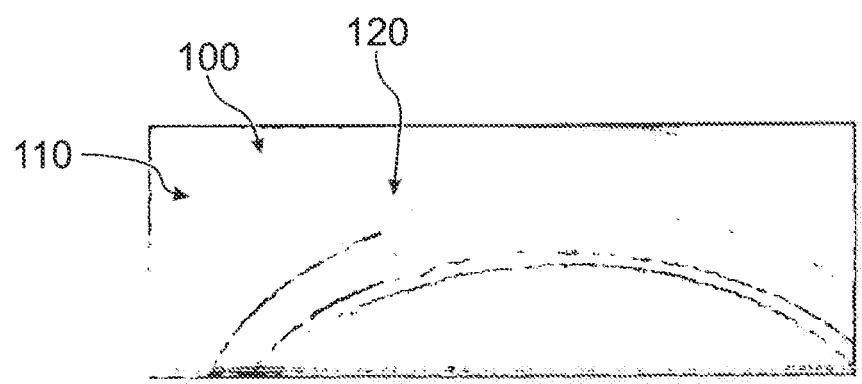

Initial testing was conducted using a retractor 100 made of a rigid, acetal ring, similar to the one pictured in FIG. 7A. Testing was performed placing retractor 100 between two halves of a liver. As shown in FIG. 9A, the acetal prototype retractor 100 comprises an inlet 120.

Figure 9B:
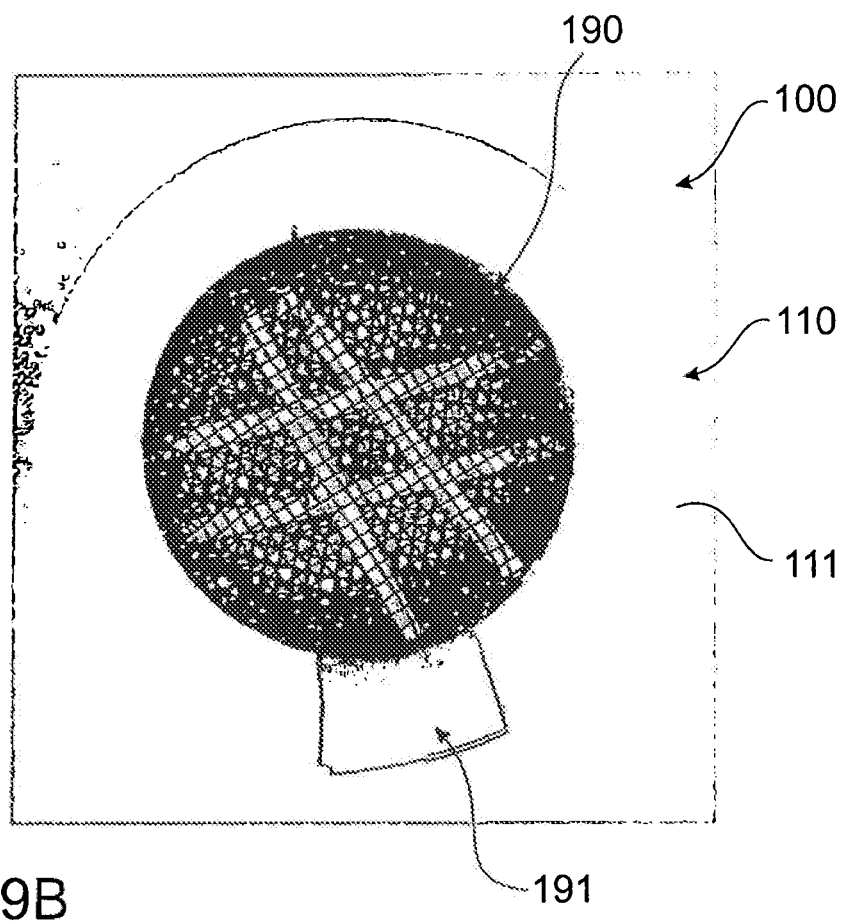

A spacer 190 comprising a wire mesh disc placed in the middle of the acetal continuous dam 110 aided in separation of the two pieces of liver, therefore maximising the area of liver surface exposed to the vacuum, see spacer 190 shown in FIG. 9B. This proved to be successful.

Figure 7B:
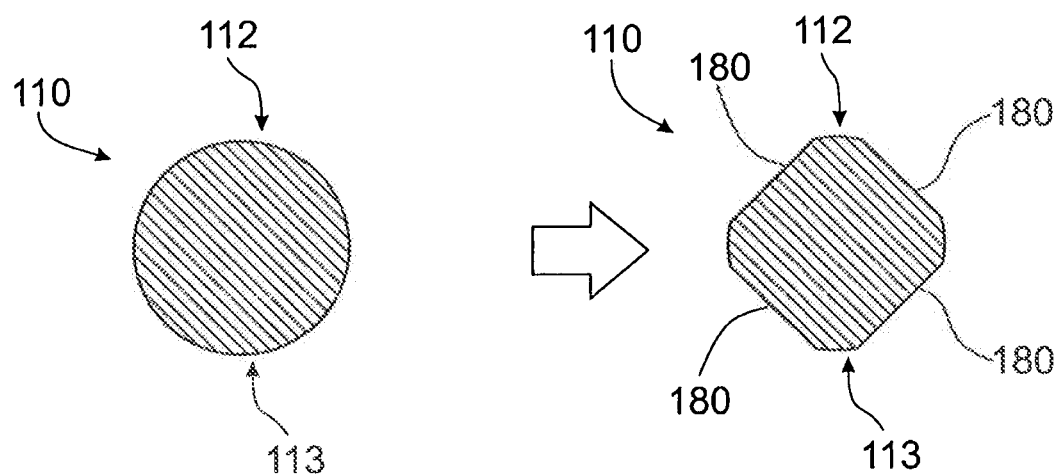

The increased force acting on the liver surface by the vacuum meant the hard edges of the acetal ring were causing impressions and tissue damage to the surface of the liver. A chamfer 180 was inserted on the walls 112, 113 to reduce this damage. FIG. 7A shows the acetal prototype retractor 100 and FIG. 7B shows the cross-sectional shape change with addition of chamfer 180. This had very little effect upon the suction results as the retractor 100 still maintained a seal on the liver.

Figure 8:
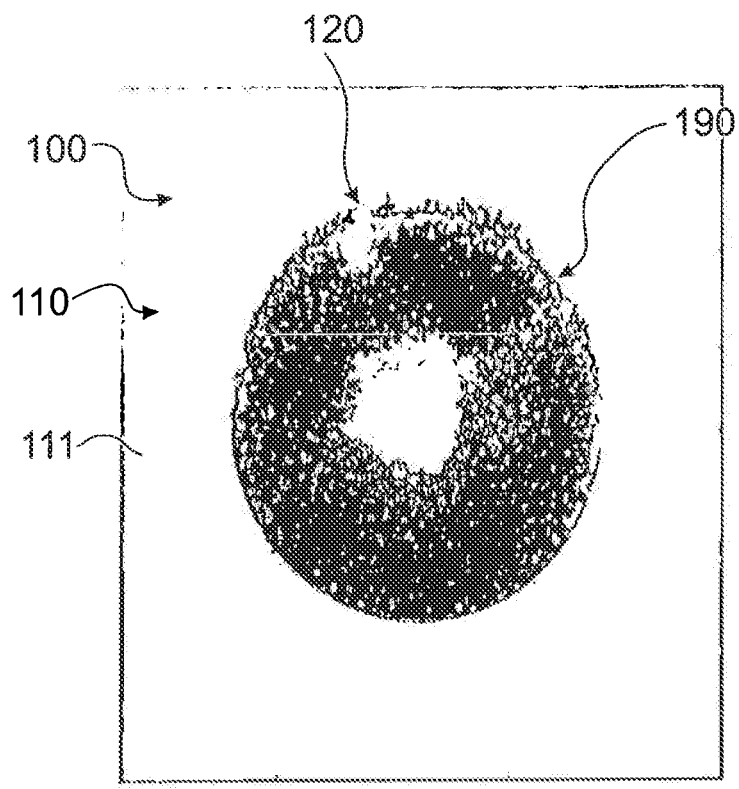

Testing then began using a spacer 190 comprising one or more low-density foam as a means of separating the liver instead of the wire mesh spacer 190. A variety of foam materials as well as foam shapes were tested. One variation is shown in FIG. 8 in which spacer 190 is a disc shaped foam placed in internal area 150 with a cut out at port 120 and a central orifice. It was concluded that no foams worked as effectively as the wire mesh insert spacer 190 because the liver compressed the material when under vacuum and also was sucked into inlet 120.

A needle valve (not shown) was attached to the suction apparatus 160 to vary the flow rate and it was found that once initial suction was created, the retractor 100 only failed once the flow was almost zero. Lowering flow rate before the initial seal is created only lengthened the time taken to create the vacuum.

The acetal retractor 100 was then machined to feature a channel or an undercut 121 through the middle of the inner face, see FIG. 9A. The section directly in front of inlet 120 was then covered by a guard 191 comprising thin tape (see FIG. 9B). Guard 191 prevented the liver from obstructing inlet 120. The results were also enhanced by having an exposed vacuum void within the undercut channel 121.

An additional retractor 100 was created to contain ridges 192 of progressive height upon the contact surfaces of dam 110 (not shown). It was hypothesised that a seal could be created on the outermost ridge, then if a part of the seal fails as the liver peels away under the force of gravity, it would seal again on the next ridge. It was concluded that this was not successful as the initial seal was always made upon the innermost edge.

Adding fenestrations 121a by a variety of means such as taping the edges and inserting brass tubing (not shown) into channel 121 seemed to create a slightly more directional flow of air through the vacuum, the overall effect was however minimal.

Figure 10:
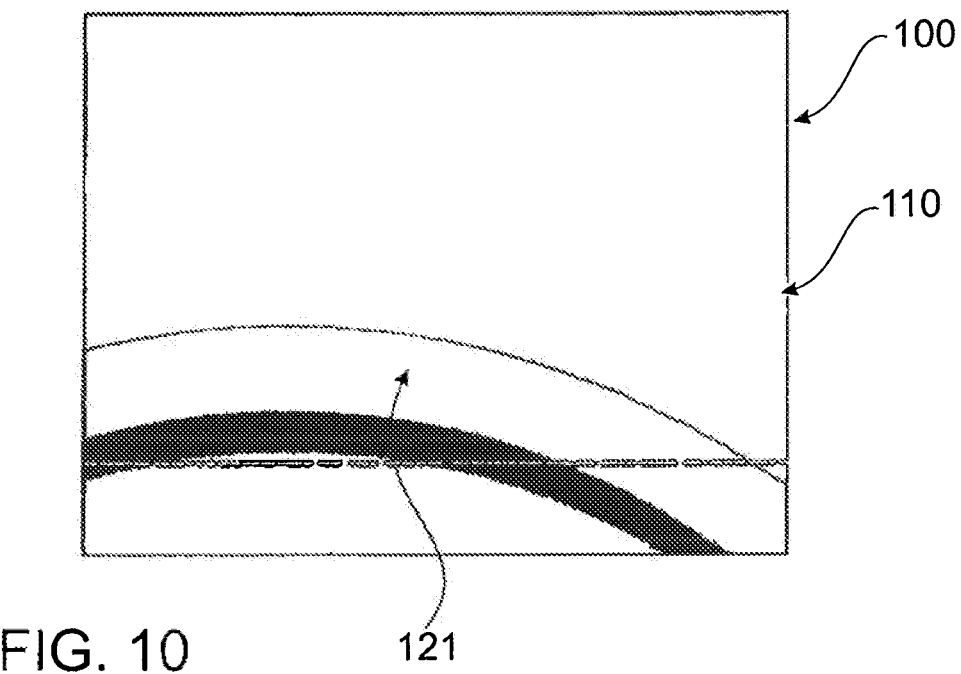

The role of the wire mesh spacer 190 was then investigated further, using substitutes such as sink strainers and fibreglass mesh, see FIGS. 10A and 10B. The effects upon the surface of the liver over time were then observed. It was determined that minor damage to the liver in the form of 'bruise like' markings, and impressions upon surface that quickly fade were not of great concern in the design. More severe damage such as blistering and tearing is to be avoided. It was observed that it was not necessarily the separating surface that caused the damage, but rather the distance the liver is able to move into the voids.

Figure 11A:
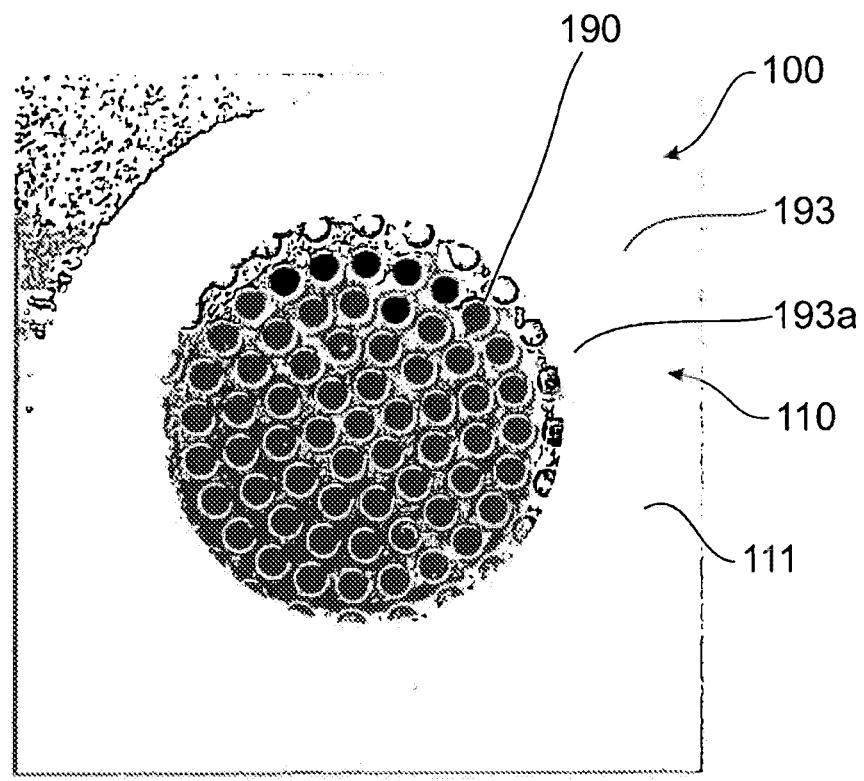
Figure 11B:
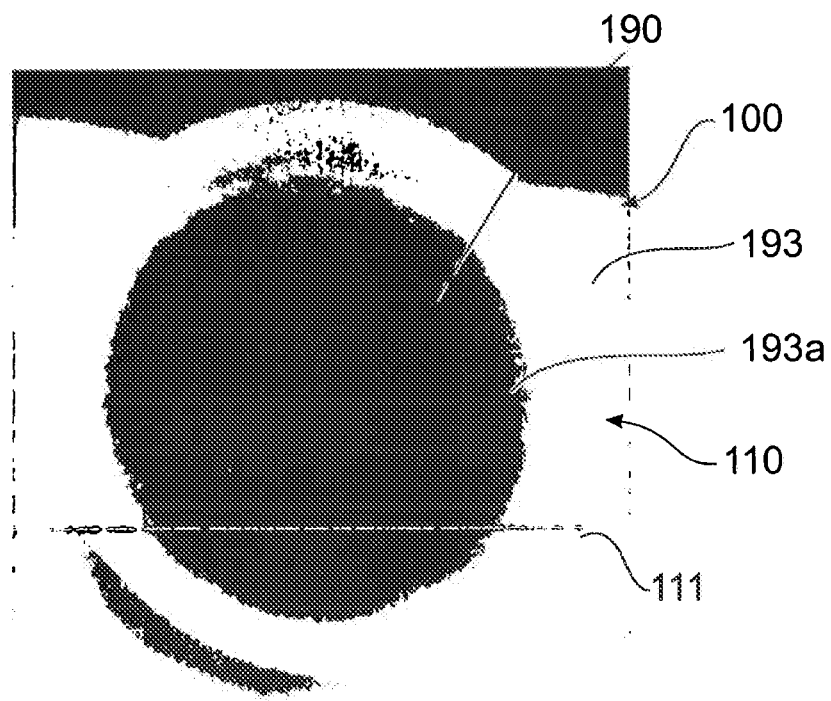

The effect of a lip 193 on walls 112, 113 was then tested, see FIGS. 11A and 11B. It was found that there is a bias to the contact surface being on the very inner edge of the walls 112, 113 or dam 110, so wide lips 193 do not act as seal faces. The lip 193 in this embodiment was formed of silicone and thereby was pliant and found to be more compliant to a slightly uneven surface, creating a better quality of seal compared to previous testing using hard parts.

It was also observed that elevating the contact face of dam 110 from the spacer 190 enhanced the vacuum effect as this was exposing the liver surface to a greater area of vacuum.

Example 3

Rapid Prototyping

Prototypes 1, 2, 3 and 4

The results of four prototypes, 1, 2, 3, 4 shown in FIGS. 12A, 12B, 12C and 12D, respectively, in creating a seal with a liver are discussed below.

Figure 12A:
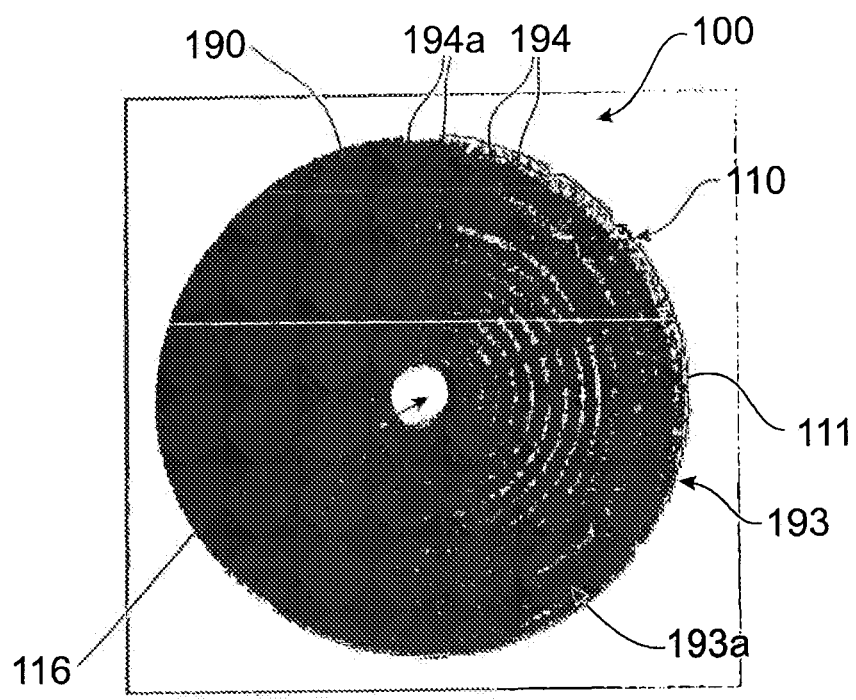

As shown in FIG. 12A prototype 1 is circular and has a spacer 190 comprising a series of radial or concentric spacing ribs 194 separated by radial or concentric grooves 194a.

Prototype 1 also comprises a central orifice 116. Prototype 1 additionally features a flexible outer lip 193 and a more rigid turreted inner lip 193a.

Figure 12B:
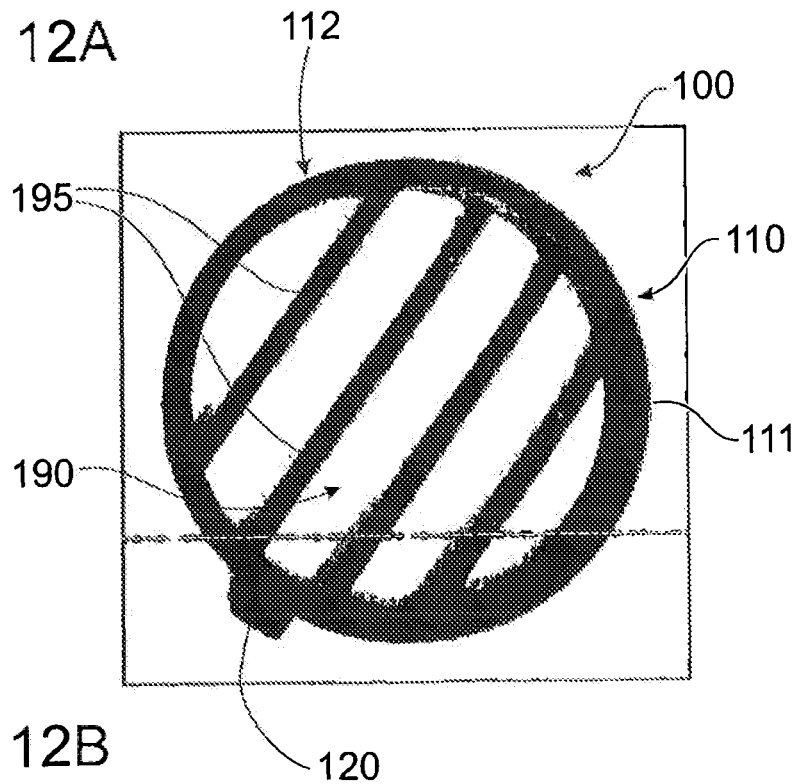

FIG. 12B shows prototype 2 which is circular and has rigid outer walls 112, 113, a spacer 190 comprising a series of parallel spacing ribs 195 with small grooves (not visible) along their length and inlet 120 which extends slightly on the exterior of dam 110. The spacing ribs 195 are graduated to allow maximum spacing in the centre.

Figure 12C:
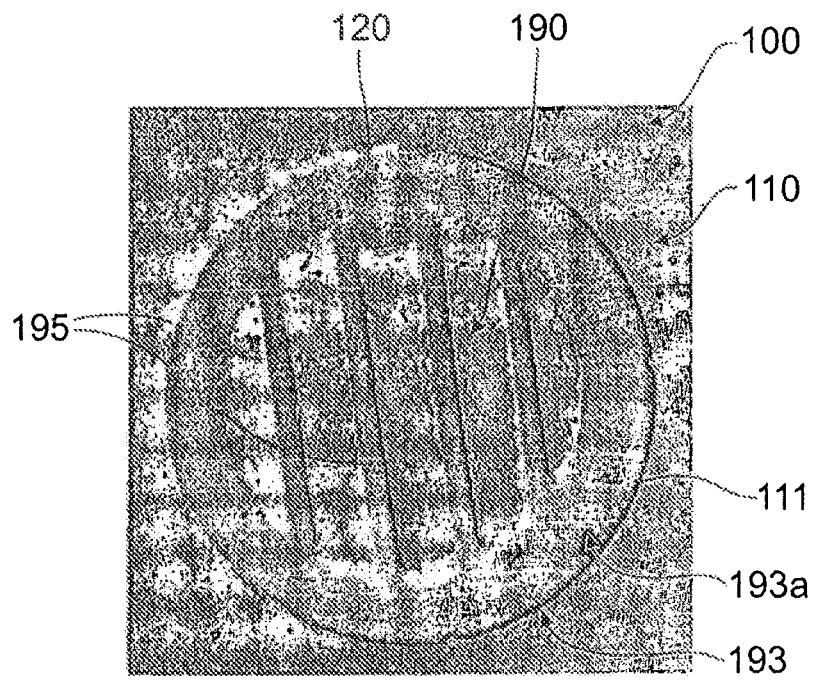

FIG. 12C shows prototype 3 which is circular and has a spacer 190 comprising a series of parallel spacing ribs 195 with small grooves (not visible) along their length and inlet 120 which extends slightly on the interior of dam 110. Prototype 3 also features a flexible outer lip 193 and a more rigid turreted inner lip 193a.

Figure 12D:
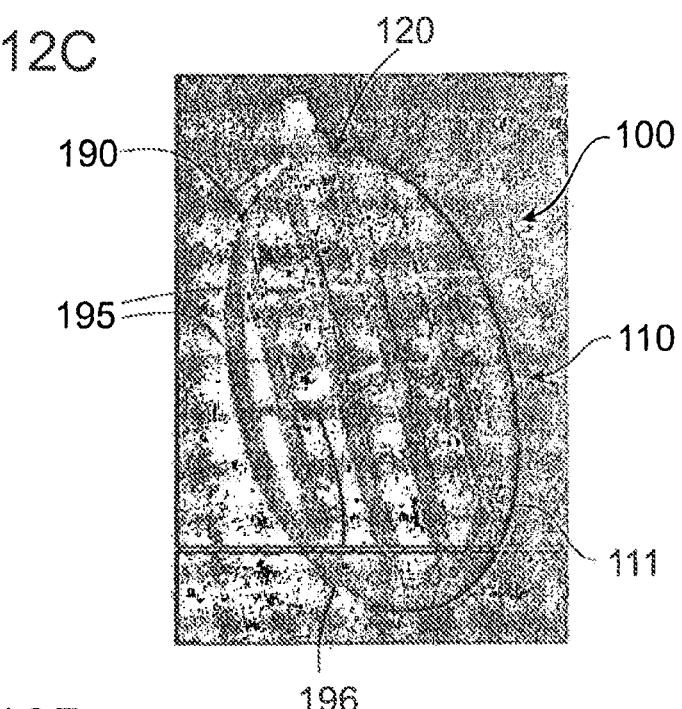

FIG. 12D shows prototype 4 which is elliptical and has rigid outer walls 112, 113, a series of parallel spacing ribs 195 with small grooves (not visible) along their length and a central transverse spacing rib 196 connecting the parallel spacing ribs 195. Transverse spacing rib 196 is curvilinear.

The testing was filmed and video footage stored.

All prototypes created a seal with the liver, although the inlets for these rapid prototypes projected well into the inner perimeter of the dam, leading to a tendency for tissue (liver) to be sucked into the inlet, thereby impeding suction distribution within the dam. Future prototypes will have the inlets recessed.

Prototype 1 and 3 retractors 100 both had identical outer wall structures of a thin, flexible outer lip 193, with more rigid turreted inner lip 193a. This flexible outer lip 193 followed the contours of the liver, with the more rigid inner turreted lip 193a providing support to the retractor 100.

Studies were performed with tubing 130 comprised of both silicone and polytetrafluoroethylene (PTFE). The silicone tubing 130 appears to be best suited as it is flexible, has minimal impact on the contact surface and seal of model. Additionally, the flow rate of the tubing of 3 mm ID was sufficient, and could possibly be decreased if possible.

The PTFE tubing 130 was not as effective as the rigidity limited the placement options, and impacted the quality of the seal as it transferred forces onto the suction ring.

Suction tubing is introduced so as to achieve suction forces within the inner confines of the dam. It has been observed that bodily tissues (for example, liver or diaphragm) tend to be drawn into the point of maximum suction forces, at the suction inlet 120. If this happens, then suction is lost within the remainder of the confines of the dam, resulting in loss of apposition. A variety of strategies can be employed to prevent this from happening, with the view to evening out the suction forces within the confines of the dam. Such strategies include a deep gutter 122 on the inner perimeter of the dam, and structures within this inner perimeter such as one or more rib 125, 126 which may be fenestrated in continuity with the suction applied; a membrane 114 which may comprise multiple perforations 115 in continuity with the suction applied; one or more spacer 190 which may comprise one or more radial ribs 194, parallel ribs 195 and/or transverse ribs 195; and/or a guard 191.

The challenge in upper gastro-intestinal SILS is exposure of the organs under the liver without resorting to additional ports. The retractor 100 and method 200 of the invention provide a simpler means of retracting the liver upwards. In this way, although not limited thereto the present retractor 100 and method 200 greatly simplifies upper Gastrointestinal (GI) surgery whether using true SILS or conventional multi-port laparoscopic surgery.

As well as the advantages of the invention elucidated above, it is clear that retractor 100, method 200 and method 300 greatly simplify complicated surgical techniques and offer a rapidity of use not previously provided.

As elucidated above, a variety of sizes and shapes of the dam may be utilised. Although not restricted thereto prototype testing has shown that a dam 110 comprising a ring is most stable.

Advantageously, retractor 100 may be used as a stand-alone device, or incorporated into a range of existing single-incision laparoscopic ports. Retractor 100 is conceived as being able to be introduced directly into the peritoneal cavity through the surgical incision, or conversely, in a collapsible form through a laparoscopic port. In the latter embodiment, the dam would expand to its desired shape by memory or potentially inflatable structures. The device could be supplied for use through standard operating theatre suction devices, or through a stand-alone suction device designed to monitor and maintain suction within pre-determined settings.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, industrial, patent and scientific literature referred to herein is incorporated herein by reference.

The invention claimed is:

1. A suction retractor comprising:
a flexible continuous dam which forms a closed loop of any shape and which defines one or more inlet, the one or more inlet communicating with a channel which extends about the closed loop, the channel configured to introduce suction into an interior area surrounded and defined by an inner perimeter of the closed loop, a guard disposed interiorly of the inner perimeter of the closed loop at least covering or partially covering the one or more inlet so that suction can be applied through the one or more inlet and into the interior area of the continuous dam, the closed loop defining opposing first and second faces extending about the interior area, the dam being sufficiently flexible so that the first and second faces may each bend while the first and second faces simultaneously conformationally engage in apposition adjacent body tissue in face-to-face sealing engagement, wherein, the one or more inlet being configured to introduce sufficient suction that, with the first and second faces being in face-to-face sealing engagement with adjacent body tissue, the adjacent body tissue is drawn towards the interior area with the guard preventing the adjacent body tissue from being drawn into the one or more inlet.

2. The suction retractor of claim 1 further comprising a suction tube defining a suction channel, the suction tube attached to or attachable to the continuous dam and when attached the suction channel continuous with the one or more inlet and the suction tube disposed laterally on the continuous dam.

3. The suction retractor of claim 2 wherein the continuous dam is planar or substantially planar and the continuous dam and the suction tube are in a planar or substantially planar arrangement.

4. The suction retractor of claim 1 wherein the channel being continuous throughout an interior of the closed loop.

5. The suction retractor of claim 1 wherein the channel comprises an open channel.

6. The suction retractor of claim 1 wherein the channel comprises a plurality of fenestrations.

7. The suction retractor of claim 1 wherein the flexible continuous dam comprises a first compacted configuration for insertion and a second open configuration for retraction wherein a shape memory allows the retractor to return to the second open configuration after being compacted.

8. A method of retracting one or more body part, tissue, organ or part thereof using the suction retractor of claim 1.

9. The suction retractor of claim 1 wherein the suction retractor is a conventional or single incision laparoscopic suction retractor.

10. The suction retractor of claim 1 wherein the closed loop having a cross-sectional profile comprising one or more lip.

11. A method of retracting a body part, tissue, organ or part thereof with suction including:
applying suction through a retractor, the retractor comprising one or more inlet defined in a flexible continuous dam, the continuous dam forming a closed loop of any shape and the one or more inlet communicating with a channel which extends about the closed loop, the channel configured to introduce suction into an interior area surrounded and defined by an inner perimeter of the closed loop, a guard disposed interiorly of the inner perimeter of the closed loop at least covering or partially covering the one or more inlet so that suction can be applied through the one or more inlet and into the interior area of the continuous dam, the closed loop defining opposing first and second faces extending about the interior area, the dam being sufficiently flexible so that the first and second faces may each bend while the first and second faces simultaneously conformationally engage in apposition adjacent body tissue face-to-face sealing engagement, wherein, the one or more inlet being configured to introduce sufficient suction that, with the first and second faces being in face-to-face sealing engagement with adjacent body tissue, the adjacent body tissue is drawn towards the interior area with the guard preventing the adjacent body tissue from being drawn into the one or more inlet, to thereby form a seal to the one or more body part, tissue, organ or part thereof and retract the one or more body part, tissue, organ or part thereof.

12. The method of claim 11 further including the step of applying suction through a suction tube attached to the continuous dam wherein the suction tube defines a suction channel continuous with the one or more inlet.

13. The method of claim 12 wherein when the suction tube is attached to the continuous dam, the suction tube is disposed laterally on the continuous dam.

14. The method of claim 12 wherein the continuous dam is planar or substantially planar and the continuous dam and the suction tube are in a planar or substantially planar arrangement.

15. The method of claim 11 wherein the channel being continuous throughout an interior of the closed loop.

16. The method of claim 15 wherein the channel comprises an open channel.

17. The method of claim 15 wherein the channel comprises a plurality of fenestrations.

18. The method of claim 11 wherein the flexible continuous dam comprises a first compacted configuration for insertion and a second open configuration for retraction wherein a shape memory allows the retractor to return to the second open configuration after being compacted.

19. The method of claim 11 wherein the suction retractor is a conventional or single incision laparoscopic suction retractor.

20. The method of claim 11 wherein the closed loop having a cross-sectional profile comprising one or more lip.

21. A method of manufacturing a suction retractor including:
forming a flexible continuous dam which forms a closed loop of any shape and which defines one or more inlet communicating with a channel which extends about the closed loop, the channel configured to introduce suction into an interior area surrounded and defined by an inner perimeter of the closed loop, a guard disposed interiorly of the inner perimeter of the closed loop at least covering or partially covering the one or more inlet so that suction can be applied through the one or more inlet and into the interior area of the continuous dam, the closed loop defining opposing first and second faces extending about the interior area, the dam being sufficiently flexible so that the first and second faces may each bend while the first and second faces simultaneously conformationally engage in apposition adjacent body tissue in face-to-face sealing engagement, wherein, the one or more inlet being configured to introduce sufficient suction that, with the first and second faces being in face-to-face sealing engagement with adjacent body tissue, the adjacent body tissue is drawn towards the interior area with the guard preventing the adjacent body tissue from being drawn into the one or more inlet.

22. The method of claim 21 further including forming or attaching a suction tube defining a suction channel so that the suction channel and one or more inlet are continuous wherein the suction tube is disposed laterally on the continuous dam.

23. A system for retracting a body part, tissue, organ and/or part thereof comprising:
a flexible continuous dam forming a closed loop of any shape and defining one or more inlet through which suction can be applied, the one or more inlet communicating with a channel which extends about the closed loop, the channel configured to introduce suction into an interior area surrounded and defined by an inner perimeter of the closed loop, a guard disposed interiorly of the inner perimeter of the closed loop at least covering or partially covering the one or more inlet so that suction can be applied through the one or more inlet and into the interior area of the continuous dam, the closed loop defining opposing first and second faces extending about the interior area, the dam being sufficiently flexible so that the first and second faces may each bend while the first and second faces simultaneously conformationally engage in apposition adjacent body tissue in face-to-face sealing engagement, wherein, the one or more inlet being configured to introduce sufficient suction that, with the first and second faces being in face-to-face sealing engagement with adjacent body tissue, the adjacent body tissue is drawn towards the interior area with the guard preventing the adjacent body tissue from being drawn into the one or more inlet; and
a suction tube disposed laterally on the continuous dam, the suction tube defining a suction channel, the suction tube attached to or attachable to the continuous dam wherein when attached the suction channel is continuous with the one or more inlet.

24. The system of claim 23 further comprising an apparatus for applying suction through the suction tube and the one or more inlet.

25. The system of claim 23 wherein the suction retractor is a conventional or single incision laparoscopic suction retractor.

26. The system of claim 23 wherein the closed loop having a cross-sectional profile comprising one or more lip.

* * * * *